(12) United States Patent
Look et al.

(10) Patent No.: US 10,716,583 B2
(45) Date of Patent: Jul. 21, 2020

(54) SYSTEMS AND METHODS FOR REMOVAL OF BLOOD AND THROMBOTIC MATERIAL

(71) Applicant: WALK VASCULAR, LLC, Irvine, CA (US)

(72) Inventors: David M. Look, Newport Beach, CA (US); Mark Mallaby, Oceanside, CA (US); Bradley S. Culbert, Mission Viejo, CA (US)

(73) Assignee: Walk Vascular, LLC, Irvine, CA (US)

( * ) Notice: Subject to any disclaimer, the term of this patent is extended or adjusted under 35 U.S.C. 154(b) by 92 days.

(21) Appl. No.: 15/493,584

(22) Filed: Apr. 21, 2017

(65) Prior Publication Data
US 2017/0216503 A1    Aug. 3, 2017

Related U.S. Application Data

(63) Continuation of application No. 14/715,451, filed on May 18, 2015, now Pat. No. 9,883,877.
(Continued)

(51) Int. Cl.
*A61B 17/22*    (2006.01)
*A61M 5/145*    (2006.01)
(Continued)

(52) U.S. Cl.
CPC ........ *A61B 17/22* (2013.01); *A61B 17/32037* (2013.01); *A61M 1/0035* (2014.02);
(Continued)

(58) Field of Classification Search
CPC .. A61B 17/22; A61B 17/32037; A61M 5/145; A61M 1/0058; A61M 5/1452; A61M 5/14216
See application file for complete search history.

(56) References Cited

U.S. PATENT DOCUMENTS 1,114,268 A    10/1914    Kells
1,148,093 A    7/1915    Kells
(Continued)

FOREIGN PATENT DOCUMENTS

CN    201079629 Y    7/2008
CN    201603160 U    10/2010
(Continued)

OTHER PUBLICATIONS

Franetzki, M., "Confusion in the Terminology of Insulin Devices", Diabetes Care, Jan.-Feb. 1982, pp. 74-75, vol. 5, No. 1, American Diabetes Association, Alexandria, USA.
(Continued)

*Primary Examiner* — Bradley J Osinski
(74) *Attorney, Agent, or Firm* — Blair Walker IP Services, LLC

(57) ABSTRACT

A system for aspirating thrombus includes a catheter having a supply lumen having a distal end and an aspiration lumen configured to couple to a vacuum source and having an interior wall surface and an open distal end, an orifice at or near the distal end of the supply lumen, in fluid communication with the interior of the aspiration lumen, the orifice located proximally of the open distal end of the aspiration lumen, wherein the orifice is configured to create a spray pattern that impinges on the interior wall surface of the aspiration lumen when a distal end of the aspiration catheter is immersed within an aqueous environment, and a disposable tubing set having a first conduit configured to couple the supply lumen of the aspiration catheter to a fluid source, and a pump component associated with the first conduit and configured to detachably couple to a drive unit.

20 Claims, 20 Drawing Sheets

Related U.S. Application Data

(60) Provisional application No. 62/000,448, filed on May 19, 2014.

(51) Int. Cl.
*A61M 5/142* (2006.01)
*A61M 1/00* (2006.01)
*A61B 17/3203* (2006.01)

(52) U.S. Cl.
CPC ........ *A61M 1/0058* (2013.01); *A61M 1/0068* (2014.02); *A61M 1/0084* (2013.01); *A61M 5/1452* (2013.01); *A61M 5/14216* (2013.01); *A61B 2017/22039* (2013.01); *A61B 2017/22079* (2013.01); *A61B 2017/22084* (2013.01); *A61B 2217/005* (2013.01); *A61B 2217/007* (2013.01); *A61M 1/0031* (2013.01); *A61M 2209/10* (2013.01)

(56) References Cited

U.S. PATENT DOCUMENTS

| | | |
|---|---|---|
| 2,804,075 A | 8/1957 | Borden |
| 3,429,313 A | 2/1969 | Romanelli |
| 3,620,650 A | 11/1971 | Shaw |
| 3,631,847 A | 1/1972 | Hobbs, II |
| 3,693,613 A | 9/1972 | Kelman |
| 3,707,967 A | 1/1973 | Kitrilakis et al. |
| 3,916,892 A | 11/1975 | Latham, Jr. |
| 3,930,505 A | 1/1976 | Wallach |
| 3,955,573 A | 5/1976 | Hansen et al. |
| 4,299,221 A | 11/1981 | Phillips et al. |
| 4,465,470 A | 8/1984 | Keiman |
| 4,574,812 A | 3/1986 | Arkans |
| 4,638,539 A | 1/1987 | Palmer |
| 4,690,672 A | 9/1987 | Veltrup |
| 4,832,685 A | 5/1989 | Haines |
| 4,883,467 A | 11/1989 | Franetzki et al. |
| 4,898,574 A | 2/1990 | Uchiyama et al. |
| 4,998,919 A | 3/1991 | Schnepp-Pesch et al. |
| 5,011,468 A | 4/1991 | Lundquist et al. |
| 5,057,098 A | 10/1991 | Zelman |
| 5,064,428 A | 11/1991 | Cope et al. |
| 5,073,164 A | 12/1991 | Hollister et al. |
| 5,073,168 A | 12/1991 | Danforth |
| 5,091,656 A | 2/1992 | Gahn |
| 5,125,893 A | 6/1992 | Dryden |
| 5,135,482 A | 8/1992 | Neracher |
| 5,197,795 A | 3/1993 | Mahurkar et al. |
| 5,234,407 A | 8/1993 | Teirstein et al. |
| 5,248,297 A | 9/1993 | Takase |
| 5,290,247 A | 3/1994 | Crittenden |
| 5,318,518 A | 6/1994 | Plechinger et al. |
| 5,320,604 A | 6/1994 | Walker et al. |
| 5,322,504 A | 6/1994 | Doherty et al. |
| 5,324,263 A | 6/1994 | Kraus et al. |
| 5,342,293 A | 8/1994 | Zanger |
| 5,342,306 A | 8/1994 | Don Michael |
| 5,368,555 A | 11/1994 | Sussman et al. |
| 5,385,562 A | 1/1995 | Adams et al. |
| 5,395,315 A | 3/1995 | Griep |
| 5,403,274 A | 4/1995 | Cannon |
| 5,413,561 A | 5/1995 | Fischell et al. |
| 5,419,772 A | 5/1995 | Teitz et al. |
| 5,421,826 A | 6/1995 | Crocker et al. |
| 5,486,183 A | 1/1996 | Middleman et al. |
| 5,490,837 A | 2/1996 | Blaeser et al. |
| 5,496,267 A | 3/1996 | Drasler et al. |
| 5,527,274 A | 6/1996 | Zakko |
| 5,536,242 A | 7/1996 | Willard et al. |
| 5,577,674 A | 11/1996 | Altonji et al. |
| 5,606,968 A | 3/1997 | Mang |
| 5,624,394 A | 4/1997 | Barnitz et al. |
| 5,626,563 A | 5/1997 | Dodge et al. |
| 5,647,847 A | 7/1997 | Lafontaine et al. |
| 5,713,849 A | 2/1998 | Bosma et al. |
| 5,713,851 A | 2/1998 | Boudewijn et al. |
| 5,713,878 A | 2/1998 | Moutafis et al. |
| 5,730,717 A | 3/1998 | Gelbfish |
| 5,785,685 A | 7/1998 | Kugler et al. |
| 5,795,322 A | 8/1998 | Boudewijn |
| 5,810,770 A | 9/1998 | Chin et al. |
| 5,827,229 A | 10/1998 | Auth et al. |
| 5,827,243 A | 10/1998 | Palestrant |
| 5,843,022 A | 12/1998 | Willard et al. |
| 5,843,051 A | 12/1998 | Adams et al. |
| 5,855,567 A | 1/1999 | Ressemann |
| 5,868,702 A | 2/1999 | Stevens et al. |
| 5,871,462 A | 2/1999 | Yoder et al. |
| 5,885,238 A | 3/1999 | Stevens et al. |
| 5,885,244 A | 3/1999 | Leone et al. |
| 5,895,399 A | 4/1999 | Barbut et al. |
| 5,910,252 A | 6/1999 | Truitt et al. |
| 5,916,192 A | 6/1999 | Nita et al. |
| 5,921,958 A | 7/1999 | Ressemann et al. |
| 5,938,645 A | 8/1999 | Gordon |
| 5,941,871 A | 8/1999 | Adams et al. |
| 5,944,686 A | 8/1999 | Patterson et al. |
| 5,957,901 A | 9/1999 | Mottola et al. |
| 5,989,210 A | 11/1999 | Morris et al. |
| 6,001,112 A | 12/1999 | Taylor |
| 6,019,728 A | 2/2000 | Iwata et al. |
| 6,022,336 A | 2/2000 | Zadno-Azizi et al. |
| 6,096,001 A | 8/2000 | Drasler et al. |
| 6,126,635 A | 10/2000 | Simpson et al. |
| 6,129,697 A | 10/2000 | Drasler et al. |
| 6,129,698 A | 10/2000 | Beck |
| 6,146,396 A | 11/2000 | Kónya et al. |
| 6,159,230 A | 12/2000 | Samuels |
| 6,176,844 B1 | 1/2001 | Lee |
| 6,179,851 B1 | 1/2001 | Barbut et al. |
| 6,190,357 B1 | 2/2001 | Ferrari et al. |
| 6,196,989 B1 | 3/2001 | Padget et al. |
| 6,206,898 B1 | 3/2001 | Honeycutt et al. |
| 6,216,573 B1 | 4/2001 | Moutafis et al. |
| 6,224,570 B1 | 5/2001 | Le et al. |
| 6,258,061 B1 | 7/2001 | Drasler et al. |
| 6,283,719 B1 | 9/2001 | Frantz et al. |
| 6,293,960 B1 | 9/2001 | Ken |
| 6,375,635 B1 | 4/2002 | Moutafis et al. |
| 6,471,683 B2 | 10/2002 | Drasler et al. |
| 6,481,439 B1 | 11/2002 | Lewis et al. |
| 6,488,672 B1 | 12/2002 | Dance et al. |
| 6,544,209 B1 | 4/2003 | Drasler et al. |
| 6,558,366 B1 | 5/2003 | Drasler et al. |
| 6,558,401 B1 | 5/2003 | Azizi |
| 6,569,148 B2 | 5/2003 | Bagaoisan et al. |
| 6,572,578 B1 | 6/2003 | Blanchard |
| 6,579,270 B2 | 6/2003 | Sussman et al. |
| 6,585,705 B1 | 7/2003 | Maginot et al. |
| 6,599,271 B1 | 7/2003 | Easley |
| 6,616,679 B1 | 9/2003 | Khosravi et al. |
| 6,622,367 B1 | 9/2003 | Bolduc et al. |
| 6,635,070 B2 | 10/2003 | Leeflang et al. |
| 6,669,710 B2 | 12/2003 | Moutafis et al. |
| 6,676,637 B1 | 1/2004 | Bonnette et al. |
| 6,719,717 B1 | 4/2004 | Johnson et al. |
| 6,723,081 B1 | 4/2004 | Hektner |
| 6,755,803 B1 | 6/2004 | Le et al. |
| 6,755,812 B2 | 6/2004 | Peterson et al. |
| 6,805,684 B2 | 10/2004 | Bonnette et al. |
| 6,818,001 B2 | 11/2004 | Wulfman et al. |
| 6,899,712 B2 | 5/2005 | Moutafis et al. |
| 6,926,726 B2 | 8/2005 | Drasler et al. |
| 6,958,059 B2 | 10/2005 | Zadno-Azizi |
| 6,986,778 B2 | 1/2006 | Zadno-Azizi |
| 6,991,625 B1 | 1/2006 | Gately et al. |
| 7,008,434 B2 | 3/2006 | Kurz et al. |
| 7,044,958 B2 | 5/2006 | Douk et al. |
| 7,122,017 B2 | 10/2006 | Moutafis et al. |
| 7,232,452 B2 | 6/2007 | Adams et al. |
| 7,374,560 B2 | 5/2008 | Ressemann et al. |
| 7,431,711 B2 | 10/2008 | Moutafis et al. |
| 7,479,147 B2 | 1/2009 | Honeycutt et al. |

(56) References Cited

U.S. PATENT DOCUMENTS

| | | |
|---|---|---|
| 7,481,222 B2 | 1/2009 | Reissmann |
| 7,588,033 B2 | 9/2009 | Wondka |
| 7,591,816 B2 | 9/2009 | Wang et al. |
| 7,604,612 B2 | 10/2009 | Ressemann et al. |
| 7,621,886 B2 | 11/2009 | Burnett |
| 7,666,161 B2 | 2/2010 | Nash et al. |
| 7,699,804 B2 | 4/2010 | Barry et al. |
| 7,717,685 B2 | 5/2010 | Moutafis et al. |
| 7,717,898 B2 | 5/2010 | Gately et al. |
| 7,736,355 B2 | 6/2010 | Itou et al. |
| 7,753,868 B2 | 7/2010 | Hoffa |
| 7,753,880 B2 | 7/2010 | Malackowski |
| 7,776,005 B2 | 8/2010 | Haggstrom et al. |
| 7,798,996 B1 | 9/2010 | Haddad et al. |
| 7,798,999 B2 | 9/2010 | Bailey et al. |
| 7,806,864 B2 | 10/2010 | Haddad et al. |
| 7,833,239 B2 | 11/2010 | Nash |
| 7,846,175 B2 | 12/2010 | Bonnette et al. |
| 7,867,192 B2 | 1/2011 | Bowman et al. |
| 7,875,004 B2 | 1/2011 | Yodfat et al. |
| 7,879,022 B2 | 2/2011 | Bonnette et al. |
| 7,887,510 B2 | 2/2011 | Karpowicz et al. |
| 7,905,710 B2 | 3/2011 | Wang et al. |
| 7,909,810 B2 | 3/2011 | Noone |
| 7,914,482 B2 | 3/2011 | Urich et al. |
| 7,914,549 B2 | 3/2011 | Morsi |
| 7,918,654 B2 | 4/2011 | Adahan |
| 7,918,822 B2 | 4/2011 | Kumar et al. |
| 7,918,835 B2 | 4/2011 | Callahan et al. |
| 7,935,077 B2 | 5/2011 | Thor et al. |
| 7,951,073 B2 | 5/2011 | Freed |
| 7,951,107 B2 | 5/2011 | Staid et al. |
| 7,951,112 B2 | 5/2011 | Patzer |
| 7,959,603 B2 | 6/2011 | Wahr et al. |
| 7,981,129 B2 | 7/2011 | Nash et al. |
| 7,998,114 B2 | 8/2011 | Lombardi |
| 8,007,490 B2 | 8/2011 | Schaeffer et al. |
| 8,012,766 B2 | 9/2011 | Graham |
| 8,021,351 B2 | 9/2011 | Boldenow et al. |
| 8,034,018 B2 | 10/2011 | Lutwyche |
| 8,043,313 B2 | 10/2011 | Krolik et al. |
| 8,062,246 B2 | 11/2011 | Moutafis et al. |
| 8,062,257 B2 | 11/2011 | Moberg et al. |
| 8,065,096 B2 | 11/2011 | Moberg et al. |
| 8,066,677 B2 | 11/2011 | Lunn et al. |
| 8,070,694 B2 | 12/2011 | Galdonik et al. |
| 8,075,546 B2 | 12/2011 | Carlisle et al. |
| 8,092,483 B2 | 1/2012 | Galdonik et al. |
| 8,123,777 B2 | 2/2012 | Krolik et al. |
| 8,140,146 B2 | 3/2012 | Kim et al. |
| 8,152,782 B2 | 4/2012 | Jang et al. |
| 8,152,951 B2 | 4/2012 | Zawacki et al. |
| 8,157,787 B2 | 4/2012 | Nash et al. |
| 8,162,877 B2 | 4/2012 | Bonnette et al. |
| 8,162,966 B2 | 4/2012 | Connor et al. |
| 8,177,739 B2 | 5/2012 | Cartledge et al. |
| 8,182,462 B2 | 5/2012 | Istoc et al. |
| 8,187,228 B2 | 5/2012 | Bikovsky |
| 8,202,243 B2 | 6/2012 | Morgan |
| 8,209,060 B2 | 6/2012 | Ledford |
| 8,221,348 B2 | 7/2012 | Hackett et al. |
| 8,246,573 B2 | 8/2012 | Ali et al. |
| 8,246,580 B2 | 8/2012 | Hopkins et al. |
| 8,257,298 B2 | 9/2012 | Hamboly |
| 8,257,343 B2 | 9/2012 | Chan et al. |
| 8,262,645 B2 | 9/2012 | Bagwell et al. |
| 8,267,893 B2 | 9/2012 | Moberg et al. |
| 8,287,485 B2 | 10/2012 | Kimura et al. |
| 8,291,337 B2 | 10/2012 | Gannin et al. |
| 8,292,841 B2 | 10/2012 | Gregersen |
| 8,308,745 B2 | 11/2012 | Sato et al. |
| 8,317,739 B2 | 11/2012 | Kuebler |
| 8,317,770 B2 | 11/2012 | Miesel et al. |
| 8,317,773 B2 | 11/2012 | Appling et al. |
| 8,317,786 B2 | 11/2012 | Dahla et al. |
| 8,323,268 B2 | 12/2012 | Ring et al. |
| 8,337,175 B2 | 12/2012 | Dion et al. |
| 8,343,097 B2 | 1/2013 | Pile-Spellman et al. |
| 8,343,131 B2 | 1/2013 | Vinten-Johansen |
| 8,348,896 B2 | 1/2013 | Wagner |
| 8,353,858 B2 | 1/2013 | Kozak et al. |
| 8,353,860 B2 | 1/2013 | Boulais et al. |
| 8,357,138 B2 | 1/2013 | Pierpont et al. |
| 8,372,038 B2 | 2/2013 | Urich et al. |
| 8,398,579 B2 | 3/2013 | Morris et al. |
| 8,398,581 B2 | 3/2013 | Panotopoulos |
| 8,398,582 B2 | 3/2013 | Gordon et al. |
| 8,414,521 B2 | 4/2013 | Baker et al. |
| 8,414,522 B2 | 4/2013 | Kamen et al. |
| 8,419,709 B2 | 4/2013 | Haddad et al. |
| 8,425,458 B2 | 4/2013 | Scopton |
| 8,430,837 B2 | 4/2013 | Jenson et al. |
| 8,430,845 B2 | 4/2013 | Wahr et al. |
| 8,430,861 B2 | 4/2013 | Schwartz et al. |
| 8,439,876 B2 | 5/2013 | Spohn et al. |
| 8,454,557 B1 | 6/2013 | Qi et al. |
| 8,465,456 B2 | 6/2013 | Stivland |
| 8,465,867 B2 | 6/2013 | Kim |
| 8,483,980 B2 | 7/2013 | Moberg et al. |
| 8,491,523 B2 | 7/2013 | Thor et al. |
| 8,506,537 B2 | 8/2013 | Torstensen et al. |
| 8,523,801 B2 | 9/2013 | Nash et al. |
| 8,529,498 B2 | 9/2013 | Moutafis et al. |
| 8,562,555 B2 | 10/2013 | MacMahon et al. |
| 8,597,238 B2 | 12/2013 | Bonnette et al. |
| 8,608,699 B2 | 12/2013 | Blomquist |
| 8,613,618 B2 | 12/2013 | Brokx |
| 8,613,724 B2 | 12/2013 | Lanier, Jr. et al. |
| 8,617,110 B2 | 12/2013 | Moberg et al. |
| 8,617,127 B2 | 12/2013 | Woolston et al. |
| 8,623,039 B2 | 1/2014 | Seto et al. |
| 8,641,671 B2 | 2/2014 | Michaud et al. |
| 8,647,294 B2 | 2/2014 | Bonnette et al. |
| 8,652,086 B2 | 2/2014 | Gerg et al. |
| 8,657,777 B2 | 2/2014 | Kozak et al. |
| 8,657,785 B2 | 2/2014 | Torrance et al. |
| 8,668,464 B2 | 3/2014 | Kensy et al. |
| 8,668,665 B2 | 3/2014 | Gerg et al. |
| 8,670,836 B2 | 3/2014 | Aeschlimann et al. |
| 8,672,876 B2 | 3/2014 | Jacobson et al. |
| 8,681,010 B2 | 3/2014 | Moberg et al. |
| 8,715,237 B2 | 5/2014 | Moberg et al. |
| 8,721,674 B2 | 5/2014 | Kusleika |
| 8,758,325 B2 | 6/2014 | Webster et al. |
| 8,783,151 B1 | 6/2014 | Janardhan et al. |
| 8,803,030 B1 | 8/2014 | Janardhan et al. |
| 8,814,892 B2 | 8/2014 | Galdonik et al. |
| 8,851,866 B2 | 10/2014 | Moutafis et al. |
| 8,932,320 B1 | 1/2015 | Janardhan et al. |
| 8,932,321 B1 | 1/2015 | Janardhan et al. |
| 8,936,447 B2 | 1/2015 | Abal |
| 8,962,561 B2 | 1/2015 | Verhoef et al. |
| 8,979,798 B2 | 3/2015 | Shener et al. |
| 8,986,252 B2 | 3/2015 | Cummings et al. |
| 9,011,114 B2 | 4/2015 | Farrell et al. |
| 9,024,768 B2 | 5/2015 | Mandro et al. |
| 9,033,925 B2 | 5/2015 | Moberg et al. |
| 9,078,691 B2 | 7/2015 | Morris et al. |
| 9,238,122 B2 | 1/2016 | Mahli et al. |
| 9,592,073 B2 | 3/2017 | Kojima et al. |
| 2001/0051811 A1 | 12/2001 | Bonnette et al. |
| 2002/0068895 A1 | 6/2002 | Beck |
| 2002/0133114 A1 | 9/2002 | Itoh et al. |
| 2002/0138095 A1 | 9/2002 | Mazzocchi et al. |
| 2002/0165575 A1 | 11/2002 | Saleh |
| 2002/0173819 A1 | 11/2002 | Leeflang et al. |
| 2002/0176788 A1 | 11/2002 | Moutafis et al. |
| 2003/0032918 A1 | 2/2003 | Quinn |
| 2003/0055404 A1 | 3/2003 | Moutafis et al. |
| 2003/0069549 A1 | 4/2003 | MacMahon et al. |
| 2003/0083681 A1 | 5/2003 | Moutafis et al. |
| 2003/0088209 A1 | 5/2003 | Chiu et al. |
| 2003/0144688 A1 | 7/2003 | Brady et al. |
| 2003/0216760 A1 | 11/2003 | Welch et al. |

(56) References Cited

U.S. PATENT DOCUMENTS

| | | |
|---|---|---|
| 2003/0220556 A1 | 11/2003 | Porat et al. |
| 2003/0236533 A1 | 12/2003 | Wilson et al. |
| 2004/0049225 A1 | 3/2004 | Denison |
| 2004/0087988 A1 | 5/2004 | Heitzmann et al. |
| 2004/0147871 A1 | 7/2004 | Burnett |
| 2004/0153109 A1 | 8/2004 | Tiedtke et al. |
| 2004/0158136 A1 | 8/2004 | Gough et al. |
| 2004/0167463 A1 | 8/2004 | Zawacki |
| 2004/0193046 A1 | 9/2004 | Nash et al. |
| 2004/0199201 A1 | 10/2004 | Kellet et al. |
| 2004/0243157 A1 | 12/2004 | Connor et al. |
| 2005/0049547 A1 | 3/2005 | Anspach et al. |
| 2005/0065426 A1 | 3/2005 | Porat et al. |
| 2005/0102165 A1 | 5/2005 | Oshita et al. |
| 2005/0159716 A1 | 7/2005 | Kobayashi et al. |
| 2005/0196748 A1 | 9/2005 | Ericson |
| 2005/0238503 A1 | 10/2005 | Rush et al. |
| 2005/0240146 A1 | 10/2005 | Nash et al. |
| 2005/0283150 A1 | 12/2005 | Moutafis et al. |
| 2006/0009785 A1 | 1/2006 | Maitland et al. |
| 2006/0063973 A1 | 3/2006 | Makower et al. |
| 2006/0064123 A1 | 3/2006 | Bonnette et al. |
| 2006/0093989 A1 | 5/2006 | Hahn et al. |
| 2006/0142630 A1 | 6/2006 | Meretei |
| 2006/0229550 A1 | 10/2006 | Staid et al. |
| 2006/0264808 A1 | 11/2006 | Staid et al. |
| 2007/0073233 A1 | 3/2007 | Thor et al. |
| 2007/0073268 A1 | 3/2007 | Goble et al. |
| 2007/0078438 A1 | 4/2007 | Okada |
| 2007/0197956 A1 | 8/2007 | Le et al. |
| 2007/0225739 A1 | 9/2007 | Pintor et al. |
| 2007/0239182 A1 | 10/2007 | Glines et al. |
| 2007/0249990 A1 | 10/2007 | Cosmescu |
| 2007/0299306 A1 | 12/2007 | Parasher et al. |
| 2008/0009784 A1 | 1/2008 | Leedle et al. |
| 2008/0097339 A1 | 4/2008 | Ranchod et al. |
| 2008/0097563 A1 | 4/2008 | Petrie et al. |
| 2008/0195058 A1 | 8/2008 | Moutafis et al. |
| 2008/0195139 A1 | 8/2008 | Donald et al. |
| 2008/0243054 A1 | 10/2008 | Mollstam et al. |
| 2008/0249501 A1 | 10/2008 | Yamasaki |
| 2008/0255596 A1 | 10/2008 | Jenson et al. |
| 2008/0294181 A1 | 11/2008 | Wensel et al. |
| 2008/0306465 A1 | 12/2008 | Bailey et al. |
| 2008/0319376 A1 | 12/2008 | Wilcox et al. |
| 2009/0054825 A1 | 2/2009 | Melsheimer et al. |
| 2009/0105690 A1 | 4/2009 | Schaeffer et al. |
| 2009/0157057 A1 | 6/2009 | Ferren et al. |
| 2009/0292212 A1 | 11/2009 | Ferren et al. |
| 2009/0306692 A1 | 12/2009 | Barrington et al. |
| 2010/0030186 A1 | 2/2010 | Stivland |
| 2010/0094201 A1 * | 4/2010 | Mallaby ........... A61B 17/32037 604/28 |
| 2010/0204672 A1 | 8/2010 | Lockhart et al. |
| 2010/0217276 A1 | 8/2010 | Garrison et al. |
| 2010/0228273 A1 | 9/2010 | Staid et al. |
| 2010/0268236 A1 | 10/2010 | Moutafis et al. |
| 2010/0274191 A1 | 10/2010 | Ting |
| 2011/0091331 A1 | 4/2011 | Moutafis et al. |
| 2011/0106019 A1 | 5/2011 | Bagwell et al. |
| 2011/0160683 A1 | 6/2011 | Pinotti Barbosa et al. |
| 2011/0282426 A1 | 11/2011 | Mitra |
| 2012/0059340 A1 | 3/2012 | Larsson |
| 2012/0123509 A1 | 5/2012 | Merrill et al. |
| 2012/0130415 A1 | 5/2012 | Tal et al. |
| 2012/0165756 A1 | 6/2012 | Root et al. |
| 2012/0259265 A1 | 10/2012 | Salehi et al. |
| 2012/0277665 A1 | 11/2012 | Tachoire et al. |
| 2012/0289910 A1 | 11/2012 | Shtul et al. |
| 2012/0291811 A1 | 11/2012 | Dabney et al. |
| 2013/0190701 A1 | 7/2013 | Kirn |
| 2013/0267891 A1 | 10/2013 | Malhi et al. |
| 2013/0310845 A1 | 11/2013 | Thor et al. |
| 2014/0005699 A1 | 1/2014 | Bonnette et al. |
| 2014/0147246 A1 | 5/2014 | Chappel et al. |
| 2014/0155931 A1 | 6/2014 | Bose et al. |
| 2014/0228869 A1 | 8/2014 | Bonnette et al. |
| 2014/0276920 A1 | 9/2014 | Hendrick et al. |
| 2014/0309589 A1 | 10/2014 | Momose et al. |
| 2014/0323906 A1 | 10/2014 | Peatfield et al. |
| 2015/0025446 A1 | 1/2015 | Jacobson et al. |
| 2015/0094673 A1 | 4/2015 | Pratt et al. |
| 2015/0094748 A1 | 4/2015 | Nash et al. |

FOREIGN PATENT DOCUMENTS

| | | |
|---|---|---|
| DE | 3715418 A1 | 11/1987 |
| EP | 806213 A1 | 11/1997 |
| EP | 726466 B1 | 4/2002 |
| EP | 1488748 A1 | 12/2004 |
| EP | 2859902 A1 | 4/2015 |
| JP | 2003260127 A | 9/2003 |
| WO | WO199005493 A1 | 5/1990 |
| WO | WO1996001079 A1 | 1/1996 |
| WO | WO1996035469 A1 | 11/1996 |
| WO | WO199918850 A1 | 4/1999 |
| WO | WO 00/69348 | 11/2000 |
| WO | WO2001037916 A1 | 5/2001 |
| WO | WO2004100772 A2 | 11/2004 |
| WO | WO2007143633 A2 | 12/2007 |
| WO | WO2008097993 A2 | 8/2008 |

OTHER PUBLICATIONS

Irsigler, K., Kritz, H., Hagmüller, G., Franezki, M., Prestele, K., Thurow, H., Geisen, K., "Long-term Continuous Intraperitoneal Insulin Infusion with an Implanted Remote-Controlled Insulin Infusion Device", Diabetes, Dec. 1981, pp. 1072-1075, vol. 30, No. 12, American Diabetes Association, New York, USA.

Kritz, H., Hagmüuller, G., Lovett, R., Irsigler, K., "Implanted Constant Basal Rate Insulin Infusion Devices for Type 1 (Insulin-Dependent) Diabetic Patients", Diabetologia, Aug. 1983, pp. 78-81, vol. 25, No. 2, Springer-Verlag, Berlin, Germany.

Micossi, P., Cristallo, M., Galiberti, G., Librenti, M., Petrella, G., Pozza, G., Hutter, R., Babic, D., Hagmuller, G., Veit, F., Irsigler, K., Walter, H., Ladik, T., Flaschentrager, T., Gunther, A., Kronski, K., Mehnert, H., Bauersachs, R., Ruhland, B., Piwernetz, K., Renner, R., Hepp, K., Buchholz, G., Kollert, D., Wohlers, C., Jahrling, P., Franetzki, M., Pfeiffer, C., Neuhauser, C., Seipke, G., Deutschländer, N., Zoltobrocki, M., "One-Year Trial of a Remote-Controlled Implantable Insulin Infusion System in Type I Diabetic Patients", The Lancet; Oct. 15, 1988, pp. 866-869, vol. 2 No. 8616, Litle, Brown, and Co. Boston, USA.

Saudek, C., Selam, J-L, Pitt, H., Waxman, K., Rubio, M., Jeandidier, N., Turner, D., Fischell, R., Charles, M., "A Preliminary trial of the Programmable Implantable Medication System for Insulin Delivery", The New England Journal of Medicine, Aug. 31, 1989, pp. 574-579, vol. 321, No. 9, Massachusetts Medical Society, Boston, USA.

Selam, J-L, "Development of Implantable Insulin Pumps: Long is the Road", Diabetic Medicine, Nov. 1988, pp. 724-733, vol. 5, No. 8, Wiley, Chichester, UK.

Dalal, J., Sahoo, P., Singh, R., Dhall, A., Kapoor, R., Krishnamurthy, A., Shetty, S., Trivedi, S., Kahali, D., Shah, B., Chockalingam, K., Abdullakutty, J., Shetty, P., Chopra, A., Ray, R., Desai, D., Pachiyappan, Ratnaparkhi, G., Sharma, M., Sambasivam, K. "Role of thrombolysis in reperfusion therapy for management of AMI: Indian scenario," Indian Heart Journal, 2013, pp. 566-585, vol. 63, Cardiological Society of India, Bombay, India.

Lipinski, M., Lee, R., Gaglia, M., Torguson, R., Garcia-Garcia, H., Pichard, A., Satler, L., Waksman, R. "Comparison of heparin, bivalirudin, and different glycoprotein IIb/IIIa inhibitor regimens for anticoagulation during percutaneous coronary intervention: A network meta-analysis," Cadiovascular Revascularization Medicine, 2016, pp. 535-545, vol. 17, Elsevier, New York, USA.

Pechlaner, C., Knapp, E., Wiedermann, C. "Hypersensitivity reactions associated with recombinant tissue-type plasminogen activator

(56) References Cited

OTHER PUBLICATIONS and urokinase," Blood Coagulation and Fibrinolysis, 2001, pp. 491-494, vol. 12, Lippincott Williams & Wilkins, Hagerstown, USA.

Principles and Practice of Pharmacology for Anaesthetists, ed. Calvey, T., Williams, N., 2008, pp. 324-327, 5th Edition, Blackwell Publishing, Malden, USA.

Puddu, P., Ianetta, L., Placanica, A., Cuturello, D., Schiariti, M., Manfrini, O. "The role of Glycoprotein IIb/IIIa inhibitors in acute coronary syndromes and the interference with anemia," International Journal of Cardiology, 2016, pp. 1091-1096, vol. 222, Elsevier, Amsterdam, The Netherlands.

Van De Werf, F. "The ideal fibrinolytic: can drug design improve clinical results?" European Heart Journal, 1999, pp. 1452-1458, vol. 20, Elsevier, Amsterdam, The Netherlands.

Warmerdam, P., Vanderlick, K., Vandervoort, P., De Smedt, H., Plaisance. S., De Maeyer, M., Collen, D. "Staphylokinase-Specific Cell-Mediated Immunity in Humans," The Journal of Immunology, 2002, pp. 155-161, vol. 168, Williams & Wilkins Co., Baltimore, USA.

CN201079629Y (Machine Translation, Sep. 7, 2018) (3 pages).
CN201603160U (Machine Translation, Sep. 7, 2018) (4 pages).
JP2003260127A (Machine Translation, Sep. 7, 2018) (5 pages).

"Comparison of Dimensions and Aspiration Rate of the Pronto V3, Pronto LP, Export XT, Export AP, Fetch, Xtract, Diver C.E. and QuickCat Catheter", Vascular Solutions, Inc., downloaded from internet Oct. 22, 2014.

Frölich, G., Meier, P., White, S., Yellon, D., Hausenloy, D., "Myocardial reperfusion injury: looking beyond primary PCI", European Heart Journal Jun. 2013, pp. 1714-1722, vol. 34, No. 23, Elsevier, Amsterdam, The Netherlands.

Gousios, A., Shearn, M, "Effect of Intravenous Heparin on Human Blood Viscosity", Circulation, Dec. 1959, pp. 1063-1066, vol. 20, American Heart Association, Dallas, USA.

"Infusion Liquid Flow Sensors—Safe, Precise and Reliable", Sensirion, downloaded from internet Apr. 3, 2015.

"Makes even the most difficult intervention a Fast and Smooth Run." GuideLiner brochure. Vascular Solutions, Inc., downloaded from internet Apr. 9, 2015.

Parikh, A., Ali, F., "Novel Use of GuideLiner Catheter to Perform Aspiration Thrombectomy in a Saphenous Vein Graft" Cath Lab Digest, Oct. 2013, downloaded from internet Oct. 22, 2014.

Prasad, A., Stone, G., Holmes, D., Gersh, B., Peperfusion Injury, Microvascular Dysfunction, and Carioprotection: The "Dark Side" of Reperfusion, Circulation, Nov. 24, 2009, pp. 2105-2112, vol. 120, American Heart Association, Dallas, USA.

Rodriquez, R., Condé-Green, A., "Quantification of Negative Pressures Generated by Syringes of Different Calibers Used for Liposuction", Plastic & Reconstructive Surgery, Aug. 2012, pp. 383e-384e, vol. 130, No. 2, Lippicott Williams & Wilkins, Philadelphia, USA.

Stys, A., Stys, T., Rajpurohit, N., Khan, M. "A Novel Application of GuideLiner Catheter for Thrombectomy in Acute Myocardial Infarction: A Case Series", Journal of Invasive cardiology, Nov. 2013, pp. 620-624, vol. 25, No. 11, King of Prussia, USA.

PCT International Search Report and Written Opinion for PCT/US2015/031460, Applicant: Walk Vascular, LLC, Forms PCT/ISA/220, 210, and 237 dated Aug. 7, 2015 (9 pages).

* cited by examiner

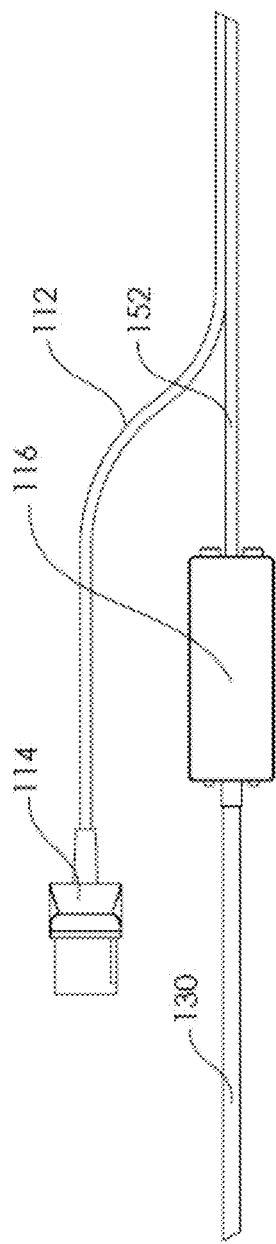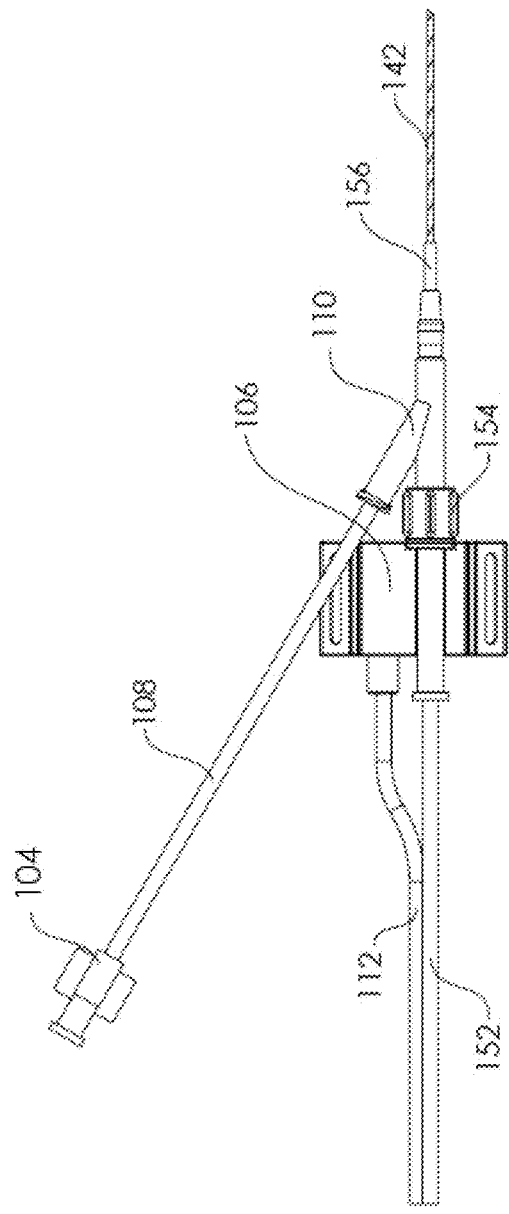

SYSTEMS AND METHODS FOR REMOVAL OF BLOOD AND THROMBOTIC MATERIAL

INCORPORATION BY REFERENCE TO ANY PRIORITY APPLICATIONS

This application is a continuation of U.S. patent application Ser. No. 14/715,451, filed on May 18, 2015, which claims the benefit of priority to U.S. Provisional Application No. 62/000,448, filed on May 19, 2014, both of which are incorporated in their entirety by reference herein for all purposes. Priority is claimed pursuant to 35 U.S.C. § 120 and 35 U.S.C. § 119.

BACKGROUND OF THE INVENTION

Field of the Invention

The present disclosure pertains generally to medical devices and methods of their use. More particularly, the present invention pertains to aspiration and thrombectomy devices and methods of use thereof.

Description of the Related Art

Several devices and systems already exist to aid in the removal of thrombotic material. These include simple aspiration tube type devices using vacuum syringes to extract thrombus into the syringe, simple flush-and-aspirate devices, more complex devices with rotating components the pull in, macerate and transport thrombotic material away from the distal tip using a mechanical auger, systems that use very high pressure to macerate the thrombus and create a venturi effect to flush the macerated material away.

All of the devices described above have limitations as a result of individual design characteristics. For example, simple aspiration catheters offer ease of use and rapid deployment but may become blocked or otherwise inoperable when faced with older, more organized thrombotic material. Such devices must be removed and cleared outside the body and then re-inserted into the vasculature, which lengthens the time needed for the procedure and increases the opportunity to kink the catheter shaft. Such kinks may reduce performance by decreasing the cross-sectional area of the catheter or may render the device inoperable.

Mechanical rotary devices use an auger to grab and carry the thrombus away from the target area. Some create transport force via vacuum bottles while others create differential pressure at the distal tip of the device with the auger acting as a low pressure pump. These devices typically work slowly and offer the physician no feedback as to when the device should be advanced further into the lesion.

Flushing type devices include manual flush type devices in which the physician manipulates a hand-driven pump to provide flowing saline at the tip of the device to break up and aspirate the thrombus material, which may introduce performance variations based on the ability of the physician to consistently pump the device over the duration of the procedure. Flushing devices also include high pressure flushing devices that macerate the thrombus and then, using a vortex created by the high pressure fluid, transport the emulsified thrombotic material to a collection bag. These devices are effective at removing all levels of thrombotic material, but the pressure created by the device is so great that its action against certain vessel walls may interrupt the heart muscle stimulation mechanism and create a bradycardia event in certain patients, sometimes requiring that a pacing lead be placed in the patient prior to use. Further, interacting with the thrombotic material outside of the catheter may allow loose material to escape the capture mechanism.

SUMMARY OF THE INVENTION

In one embodiment of the present invention, a system for aspirating thrombus includes an aspiration catheter having a supply lumen and an aspiration lumen, the supply lumen having a wall and a closed distal end, the aspiration lumen configured to couple to a vacuum source and having an interior wall surface, and an open distal end, an orifice in the wall of the supply lumen, in fluid communication with the interior of the aspiration lumen, the orifice located proximally of the open distal end of the aspiration lumen and adjacent the closed distal end of the supply lumen, wherein the orifice is configured to create a spray pattern when pressurized fluid is pumped through the supply lumen such that the spray pattern impinges on the interior wall surface of the aspiration lumen when a distal end of the aspiration catheter is immersed within an aqueous environment, and a disposable tubing set having a first conduit configured to couple to the supply lumen of the aspiration catheter to a fluid source, and a pump component associated with the first conduit and configured to detachably couple to a drive unit, such that motion from the drive unit is transferred to the pump component such that resultant motion of the pump component causes fluid from the fluid source to be injected through the supply lumen of the aspiration catheter, and through the orifice into the aspiration lumen.

In another embodiment of the present invention, a system for aspirating thrombus includes an aspiration catheter having a supply lumen and an aspiration lumen, the supply lumen having a distal end, the aspiration lumen configured to couple to a vacuum source and having an interior wall surface, and an open distal end, an orifice at or near the distal end of the supply lumen, in fluid communication with the interior of the aspiration lumen, the orifice located proximally of the open distal end of the aspiration lumen, wherein the orifice is configured to create a spray pattern when pressurized fluid is pumped through the supply lumen such that the spray pattern impinges on the interior wall surface of the aspiration lumen when a distal end of the aspiration catheter is immersed within an aqueous environment, and a disposable tubing set having a first conduit configured to couple the supply lumen of the aspiration catheter to a fluid source, and a pump component associated with the first conduit and configured to detachably couple to a drive unit, such that motion from the drive unit is transferred to the pump component such that resultant motion of the pump component causes fluid from the fluid source to be injected through the supply lumen of the aspiration catheter, and through the orifice into the aspiration lumen.

In another embodiment of the present invention, a method for delivery of a drug includes providing a catheter including a supply lumen and an aspiration lumen, the supply lumen having a distal end, the aspiration lumen configured to couple to a vacuum source and having an interior wall surface, and an open distal end, an orifice at or near the distal end of the supply lumen, in fluid communication with the interior of the aspiration lumen, the orifice located proximally of the open distal end of the aspiration lumen, wherein the orifice is configured to create a spray pattern when pressurized fluid is pumped through the supply lumen such that the spray pattern impinges on the interior wall surface of the aspiration lumen when a distal end of the aspiration catheter is immersed within an aqueous environment, providing a disposable tubing set having a first conduit configured to couple the supply lumen of the catheter to a fluid source, and a pump component associated with the first conduit and configured to detachably couple to a drive unit, such that motion from the drive unit is transferred to the pump component such that resultant motion of the pump component causes fluid from the fluid source to be injected through the supply lumen of the catheter, and through the orifice into the aspiration lumen, coupling the supply lumen of the catheter to a fluid source, wherein the fluid source contains at least a first drug for intravascular delivery, inserting the catheter within a blood vessel of a patient and advancing the catheter to a target site, coupling the pump component to a drive unit, and operating the drive unit to cause the pump component to inject at least some of the first drug in the region of the target site.

BRIEF DESCRIPTION OF THE DRAWINGS

FIG. 6 is a detailed view of detail 6 of FIG. 4.
FIG. 7 is a detailed view of detail 7 of FIG. 4.

DETAILED DESCRIPTION OF THE ILLUSTRATED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
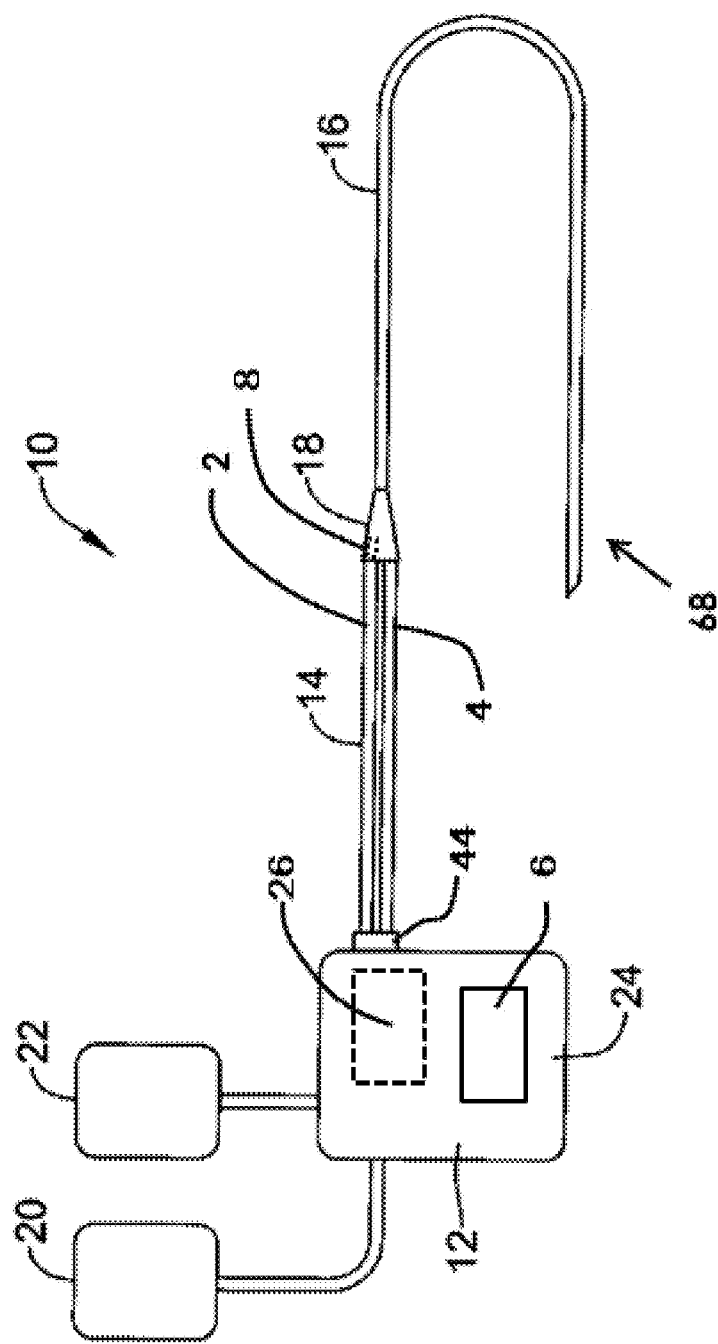
FIG. 1 is a diagrammatic view of a system for aspirating thrombus according to an embodiment of the present invention.

FIG. 1 is a diagrammatic figure depicting an assisted aspiration system 10. The aspiration system 10 includes a remote hand piece 12 that contains a fluid pump 26 and an operator control interface 6. In one contemplated embodiment, the system 10 is a single use disposable unit. The aspiration system 10 may also include extension tubing 14, which contains a fluid irrigation lumen 2 (or high pressure injection lumen) and an aspiration lumen 4, and which allows independent manipulation of a catheter 16 without requiring repositioning of the hand piece 12 during a procedure performed with the aspiration system 10. Extension tubing 14 may also act as a pressure accumulator. High pressure fluid flow from the pump 26, which may comprise a displacement pump, pulses with each stroke of the pump 26, creating a sinusoidal pressure map with distinct variations between the peaks and valleys of each sine wave. Extension tubing 14 may be matched to the pump 26 to expand and contract in unison with each pump pulse to reduce the variation in pressure caused by the pump pulses to produce a smooth or smoother fluid flow at tip of catheter 16. Any tubing having suitable compliance characteristics may be used. The extension tubing 14 may be permanently attached to the pump 26 or it may be attached to the pump 26 by a connector 44. The connector 44 is preferably configured to ensure that the extension tubing 14 cannot be attached to the pump 26 incorrectly.

Figure 3:
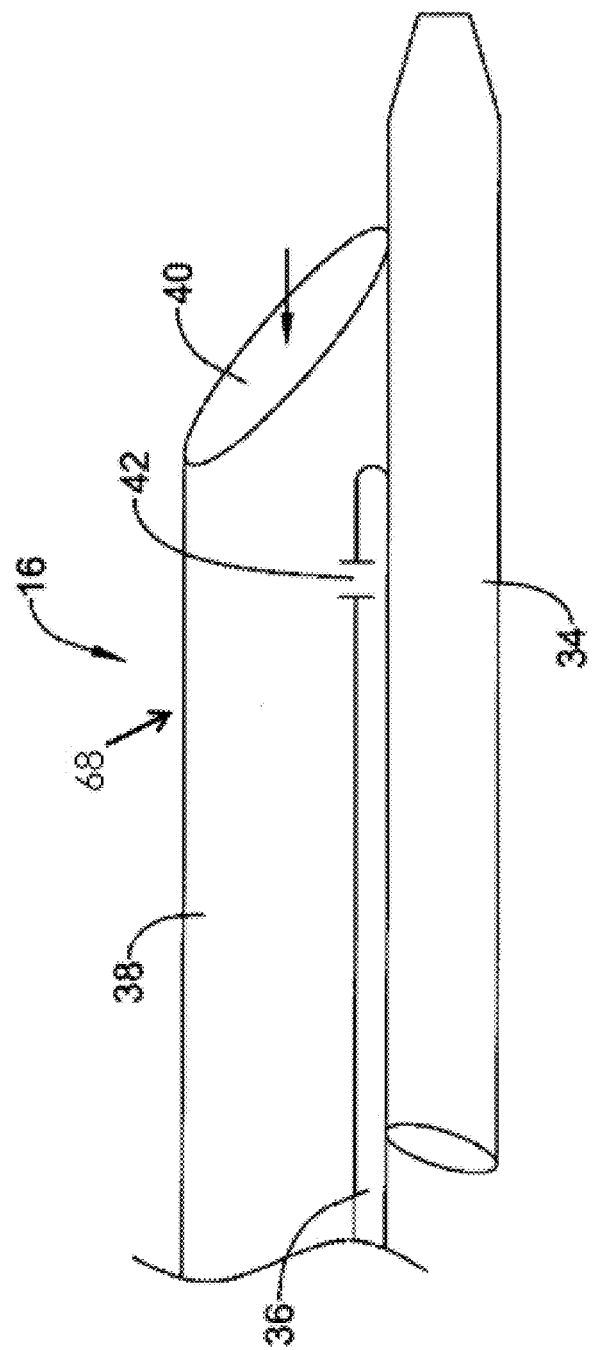
FIG. 3 is a diagrammatic view of the distal end portion of the system for aspirating thrombus of FIG. 1.

An interface connector 18 joins the extension tubing 14 and the catheter 16 together. In one contemplated embodiment, the interface connector 18 may contain a filter assembly 8 between high pressure fluid injection lumen 2 of the extension tubing 14 and a high pressure injection lumen 36 of the catheter 16 (FIG. 3). The catheter 16 and the extension tubing 14 may be permanently joined by the interface connector 18. Alternatively, the interface connector 18 may contain a standardized connection so that a selected catheter 16 may be attached to the extension tubing 14.

Attached to the hand piece 12 are a fluid source 20 and a vacuum source 22. A standard hospital saline bag may be used as fluid source 20; such bags are readily available to the physician and provide the necessary volume to perform the procedure. Vacuum bottles may provide the vacuum source 22, or the vacuum source 22 may be provided by a syringe, a vacuum pump or other suitable vacuum sources.

In one contemplated embodiment, the catheter 16 has a variable stiffness ranging from stiffer at the proximal end to more flexible at the distal end. The variation in the stiffness of the catheter 16 may be achieved with a single tube with no radial bonds between two adjacent tubing pieces. For example, the shaft of the catheter 16 may be made from a single length of metal tube that has a spiral cut down the length of the tube to provide shaft flexibility. Variable stiffness may be created by varying the pitch of the spiral cut through different lengths of the metal tube. For example, the pitch of the spiral cut may be greater (where the turns of the spiral cut are closer together) at the distal end of the device to provide greater flexibility. Conversely, the pitch of the spiral cut at the proximal end may be lower (where the turns of the spiral cut are further apart) to provide increased stiffness. In some embodiments, a single jacket may cover the length of the metal tube to provide for a vacuum tight catheter shaft. Other features of catheter 16 are described with reference to FIG. 3, below.

Figure 2:
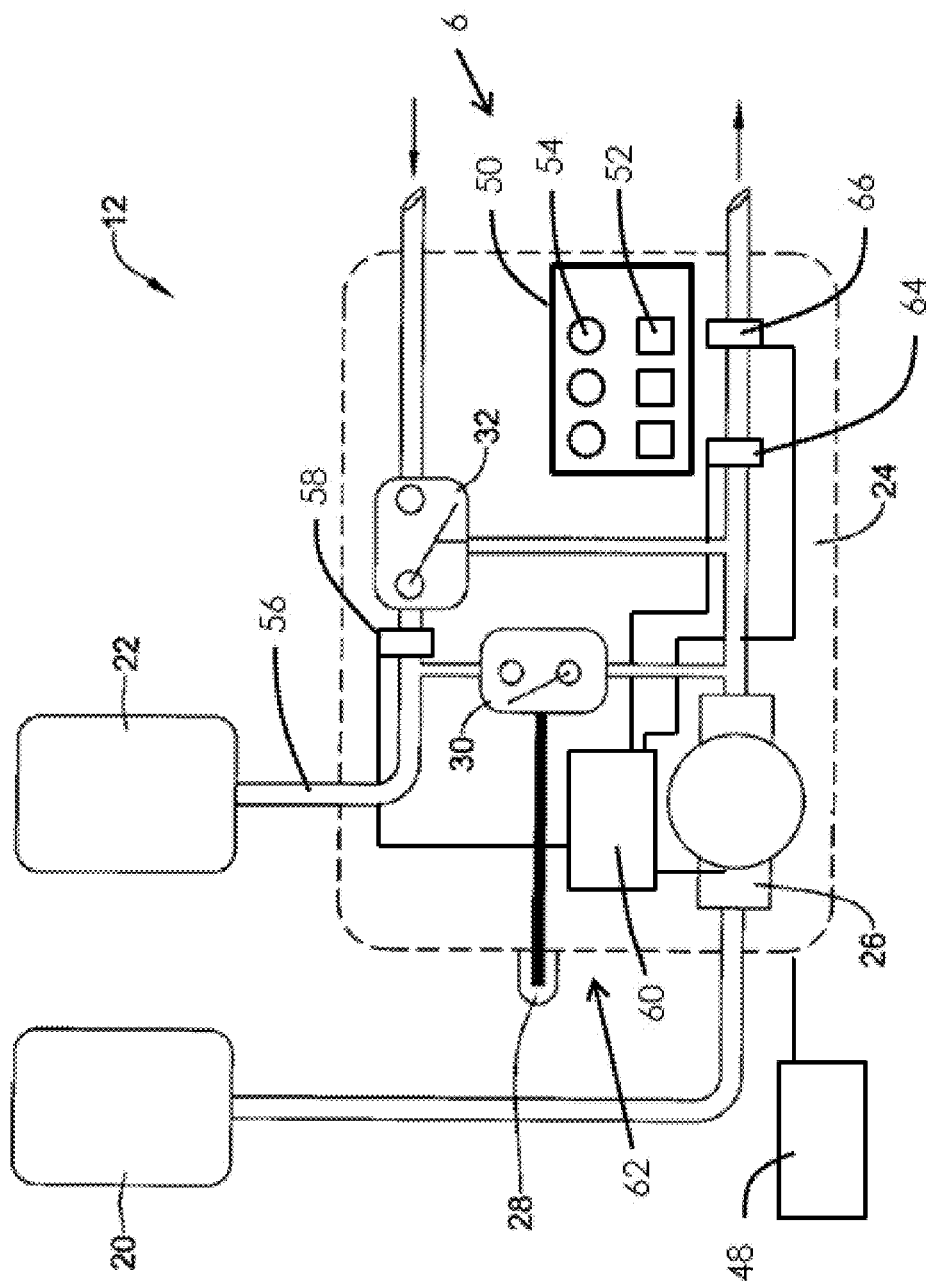
FIG. 2 is a diagrammatic view showing more detail of the proximal portion of the system for aspirating thrombus of FIG. 1.

FIG. 2 is a diagrammatic view showing more detail of the hand piece 12 and the proximal portion of assisted catheter aspiration system 10. The hand piece 12 includes a control box 24 where the power and control systems are disposed. The pump 26 may in some embodiments be a motor driven displacement pump that has a constant output. The pump displacement relationship to the catheter volume, along with the location of the orifice 42 (exit) of the catheter high pressure lumen 36 within the aspiration lumen 38 (FIG. 3), ensures that no energy is transferred to the patient from the saline pump as substantially all pressurized fluid is evacuated by the aspiration lumen. A prime button 28 is mechanically connected to a prime valve 30. When preparing the device for use, it is advantageous to evacuate all air from the pressurized fluid system to reduce the possibility of air embolization. By depressing the prime button 28, the user connects the fluid source 20 to the vacuum source 22 via the pump 26. This forcefully pulls fluid (for example 0.9% NaCl solution, or "saline", or "normal saline", or heparinized saline) through the entire pump system, removing all air and positively priming the system for safe operation. A pressure/vacuum valve 32 is used to turn the vacuum on and off synchronously with the fluid pressure system. One contemplated valve 32 is a ported one way valve. Such a valve is advantageous with respect to manual or electronic valve systems because it acts as a tamper proof safety feature by mechanically and automatically combining the operations of the two primary systems. By having pressure/vacuum valve 32, the possibility of turning the vacuum on without also activating the fluid system is eliminated.

The operator control interface 6 is powered by a power system 48 (such as a battery or an electrical line), and may comprise an electronic control board 50, which may be operated by a user by use of one or more switches 52 and one or more indicator lamps 54. The control board 50 also monitors and controls several device safety functions, which include over pressure detection, air bubble detection, and vacuum charge. A pressure sensor 64 monitors pressure (i.e. injection pressure), and senses the presence of air bubbles. Alternatively, or in conjunction, an optical device 66 may be used to sense air bubbles. In one contemplated embodiment, the pump pressure is proportional to the electric current needed to produce that pressure. Consequently, if the electric current required by pump 26 exceeds a preset limit, the control board 50 will disable the pump 26 by cutting power to it. Air bubble detection may also be monitored by monitoring the electrical current required to drive the pump 26 at any particular moment. In order for a displacement pump 26 to reach high fluid pressures, there should be little or no air (which is highly compressible) present in the pump 26 or connecting system (including the catheter 16 and the extension tubing 14). The fluid volume is small enough that any air in the system will result in no pressure being generated at the pump head. The control board monitors the pump current for any abrupt downward change that may indicate that air has entered the system. If the rate of drop is faster than a preset limit, the control board 50 will disable the pump 26 by cutting power to it until the problem is corrected. Likewise, a block in the high pressure lumen 36 (FIG. 3), which may be due to the entry of organized or fibrous thrombus, or a solid embolus, may be detected by monitoring the electrical current running the pump 26. In normal use, the current fluxuations of the pump 26 are relatively high. For example, the pump 26 may be configured so that there is a variation of 200 milliAmps or greater in the current during normal operation, so that when current fluxuations drop below 200 milliAmps, air is identified, and the system shuts down. Alternatively, current fluxuations in the range of, for example, 50 milliAmps to 75 milliAmps may be used to identify that air is in the system. Additionally, an increase in the current or current fluxuations may indicate the presence of clot or thrombus within the high pressure lumen 36. For example, a current of greater than 600 milliAmps may indicate that thrombus it partially or completely blocking the high pressure lumen 36, or even the aspiration lumen 38 (FIG. 3).

A vacuum line 56, connected to the vacuum source 22, may be connected to a pressure sensor 58. If the vacuum of the vacuum source 22 is low (i.e. the absolute value pressure has decreased) or if a leak is detected in the vacuum line 56, the control board 50 disables the pump 26 until the problem is corrected. The pressure sensor 58 may also be part of a safety circuit 60 that will not allow the pump 26 to run if a vacuum is not present. Thereby, a comprehensive safety system 62, including the safety circuit 60, the pressure sensor 64 and/or the optical device 66, and the pressure sensor 58, requires both pump pressure and vacuum pressure for the system to run. If a problem exists (for example, if there is either a unacceptably low pump pressure or an absence of significant vacuum), the control board 50 will not allow the user to operate the aspiration system 10 until all problems are corrected. This will keep air from being injected into a patient, and will assure that the aspiration system 10 is not operated at incorrect parameters. Alternatively, in lieu of a direct connection (e.g., electrical, optical), the pressure sensor 58 can be configured to send a wireless signal to the control board 50, or any other component (e.g., antenna) coupled to or in communication with the control board 50, to remotely control operation of the pump 26. The removte control may be possible, whetehr the pump is within the sterile filed or outside the sterile field.

FIG. 3 is a diagrammatic view of the distal end portion 68 of the assisted catheter aspiration system 10, showing more details of the catheter 16. The catheter 16 in some embodiments is a single-operator exchange catheter and includes a short guidewire lumen 34 attached to the distal end of the device. The guidewire lumen 34 can be between about 1 and about 30 cm in length, or between about 5 and about 25 cm in length, or between about 5 and about 20 cm in length, or approximately 13.5 cm in length. In other embodiments, a full-length guidewire lumen (extending the length of the catheter 16) may be used. For example, a catheter 16 sized to be used on peripheral blood vessels, including peripheral arteries, may incorporate a full-length guidewire lumen. In some embodiments, the aspiration itself may also serve as a guidewire lumen. An aspiration lumen 38 includes a distal opening 40 which allows a vacuum (for example, from vacuum source 22) to draw thrombotic material into the aspiration lumen 38. A high pressure lumen 36 includes a distal orifice 42 that is set proximally of distal opening 40 by a set amount. For example, distal orifice 42 can be set proximally of distal opening 40 by about 0.508 mm (0.020 inches), or by 0.508 mm±0.076 mm (0.020 inches±0.003 inches) or by another desired amount. The orifice 42 is configured to spray across the aspiration lumen to macerate and/or dilute the thrombotic material for transport to vacuum source 22, for example, by lowering the effective viscosity of the thrombotic material. The axial placement of the fluid orifice 42 is such that the spray pattern interaction with the opposing lumen wall preferably produces a spray mist and not a swirl pattern that could force embolic material out from the distal opening 40. The spray pattern may be present at least when a distal end of the catheter 16 is within an aqueous environment, such as a body lumen, including a blood vessel. The aqueous environment may be at body temperature, for example between about 35.0° C. and about 40.0° C., or between about 36.0° C. and about 38.0° C. The system may be configured so that the irrigation fluid leaves the pump at a pressure of between about 3.447 megapascal (500 pounds per square inch) and about 10.342 megapascal (1500 pounds per square inch). In some embodiments, after a pressure head loss along the high pressure lumen 36, the irrigation fluid leaves orifice 42 at between about 4.137 megapascal (600 pounds per square inch) and about 8.274 megapascal (1200 pounds per square inch), or between about 4.816 megapascal (650 pounds per square inch) and about 5.861 megapascal (850 pounds per square inch).

Figure 4:
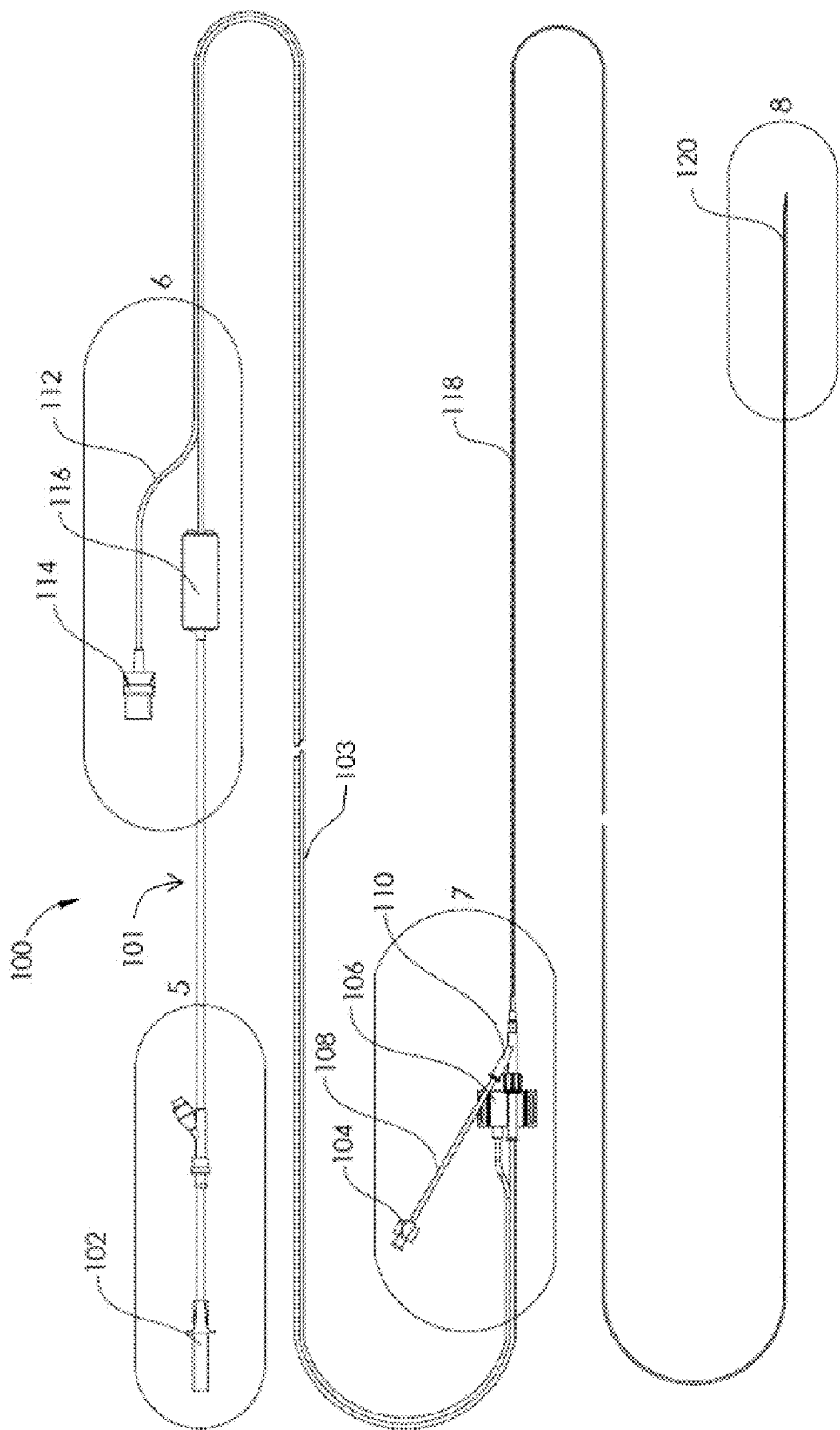
FIG. 4 is a plan view of disposable components of a system for aspirating thrombus according to an embodiment of the present invention.
Figure 12:
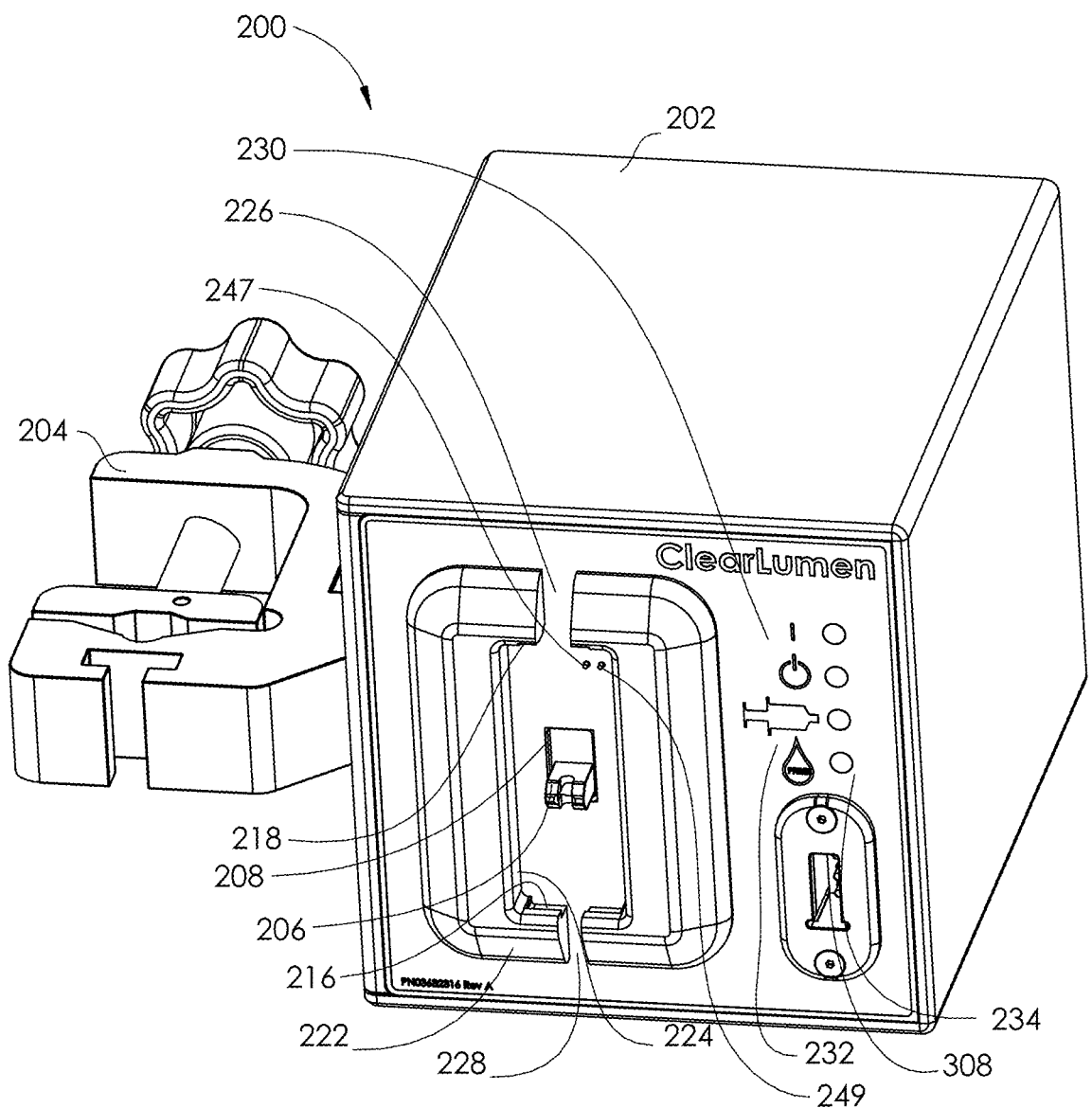
FIG. 12 is elevation perspective view of a pump base according to an embodiment of the present invention.
Figure 13:
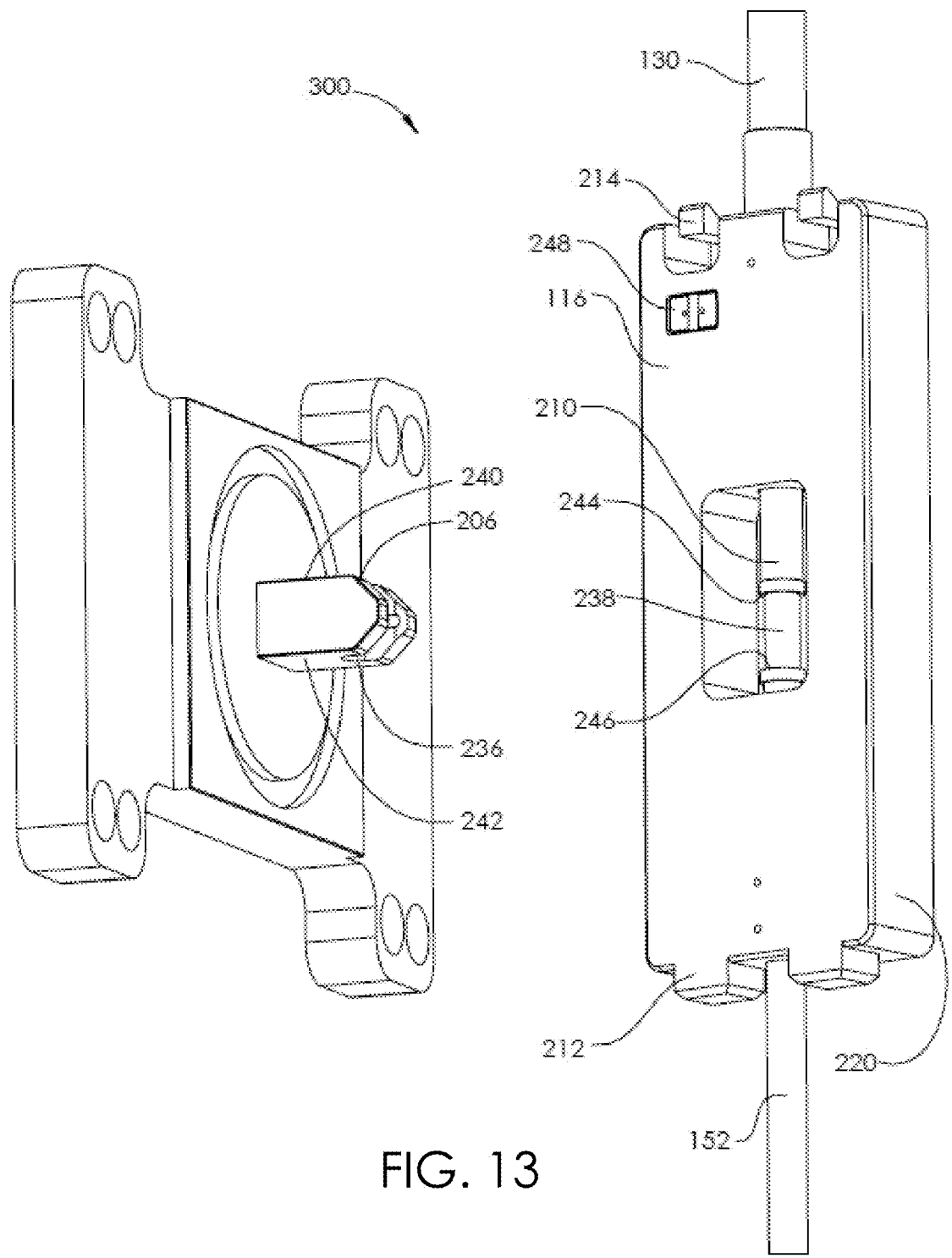
FIG. 13 illustrates a piston of the system for aspirating thrombus being coupled to a saddle of a piston pump.

FIG. 4 illustrates a system for aspirating thrombus 100 according to an embodiment of the present invention. The system for aspirating thrombus 100 depicted in FIG. 4 represents disposable components 101, comprising a tubing set 103 and an aspiration catheter 118, which are configured to attach to a vacuum source 22, a fluid source 20 (FIGS. 1 and 2), a pressure monitor (not shown), and a pump base 200 (FIG. 12). The system for aspirating thrombus 100 is also configured to be used with a guidewire. Beginning with the components of the tubing set 103, a spike 102 (shown in more detail in FIG. 5) is configured to couple to a fluid source 20 such as a saline bag. The saline bag may have a volume of saline equal to about 1000 ml or about 500 ml. The saline may be heparinized, or may contain one or more therapeutic agents. The saline may be at room temperature, or may be warmed or cooled. A connector 104 (shown in more detail in FIG. 7), for example a luer connector, is configured to couple to a vacuum source 22. The vacuum source 22 may be a vacuum bottle having a volume of between 20 ml and 500 ml. The vacuum source 22 may instead be a 60 ml syringe whose plunger is pulled back after coupling to the connector 104. This may be a lockable plunger, which is locked in order to maintain the evacuated plunger position. In some cases, the vacuum source 22 may be a 20 ml syringe or a 30 ml syringe. An exemplary syringe with a lockable plunger is the VacLok® syringe sold by Merit Medical Systems, Inc. of South Jordan, Utah, USA. The vacuum source 22 may also be a vacuum pump, with or without a collection container. A pressure transducer$_{106}$ capable of measuring vacuum (including positive pressure sensors that are configured to measure positive pressure, but are capable of measuring negative pressure) is coupled to a vacuum line 108 via a y-connector 110. Signals from the pressure transducer 106 travel along a cable 112 (FIG. 7), which also supplies voltage to the pressure transducer 106. A connector 114 (also shown in FIG. 6) couples the cable 112 to a pressure monitor or to the pump base 200. A cassette 116 is a disposable component attachable to the pump base 200 (FIG. 12) for allowing pressurized injection of a liquid injectate (such as saline). The cassette 116 is described in more detail in relation to FIG. 6. The aspiration catheter 118 having a distal end 120 is shown in more detail in FIG. 8.

Figure 5:
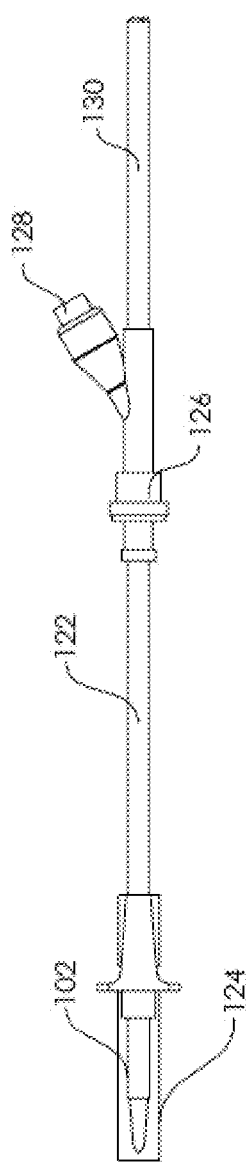
FIG. 5 is a detailed view of detail 5 of FIG. 4.

Turning to FIG. 5, the spike 102 communicates with extension tubing 122. Liquid injectate is pumped downstream at the piston pump, which pulls more liquid injectate (for example from a saline bag) through a check valve 126 and through a supply tube 130. An injection port 128 may be used for injecting other materials into the system, or for removing air or priming the system. The spike 102 may be packaged with a removable protective spike cover 124.

Figure 9:
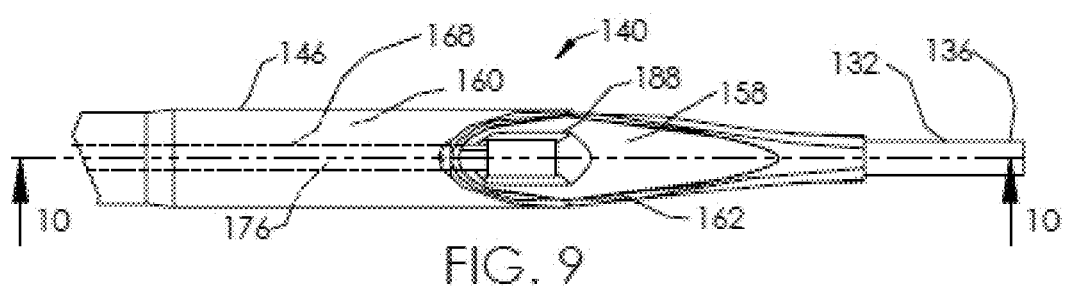
FIG. 9 is a plan view of a distal end of an aspiration catheter of the system for aspirating thrombus of FIG. 4.
Figure 10:
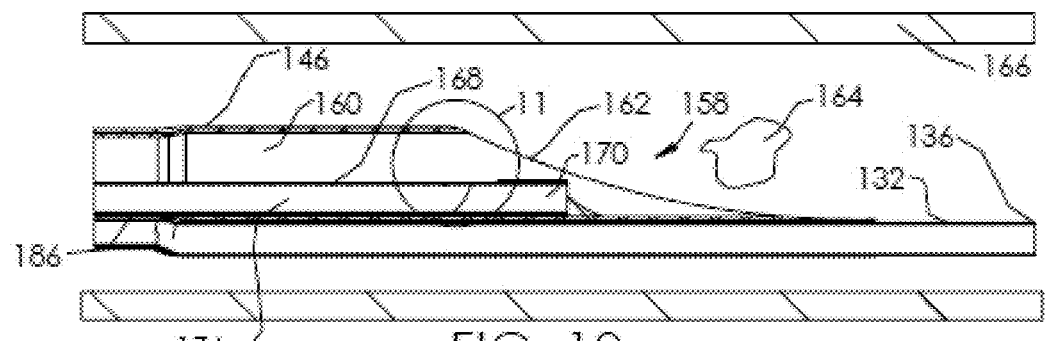
FIG. 10 is a sectional view of FIG. 9 taken through line 10-10, as viewed within a blood vessel.
Figure 11:
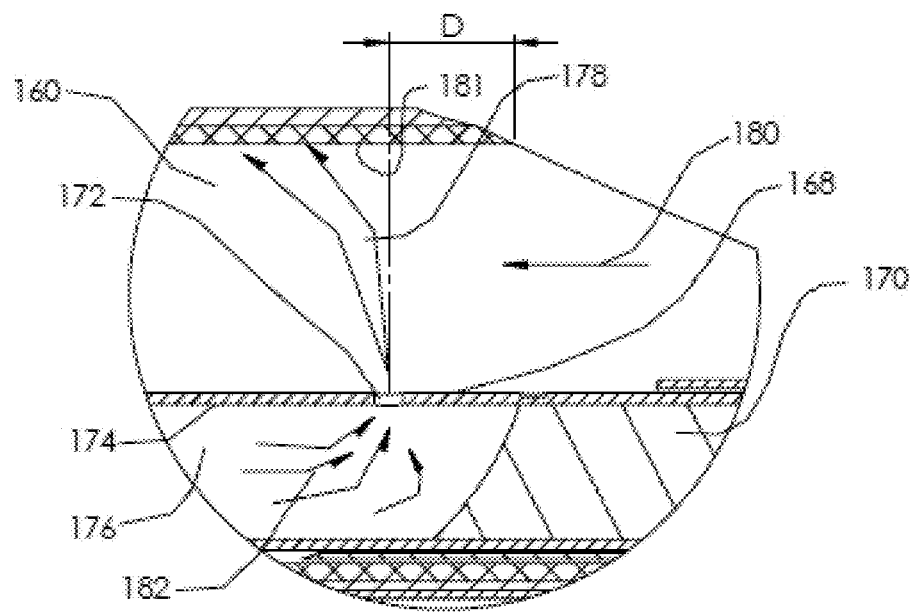
FIG. 11 is a detailed view of detail 11 of FIG. 10.

The cassette 116, as seen in FIG. 6, pulls liquid injectate from the supply tube 130, and pressurizes (in conjunction with the pump base 200) an injection tube 152. More detail of the cassette 116 will be described along with the description of the entire piston pump. FIG. 7 shows more detail of the pressure transducer 106 for measuring the vacuum. The pressure transducer 106 connects to the y-connector 110 with a luer fitting 154. The injection tube 152 and the vacuum line 108 communicate to lumens of a catheter shaft 142. For example, the injection tube 152 may be fluidly connected to a distal supply tube 168 (FIGS. 9-11), for example a polyimide or stainless steel or nitinol tube having high strength thin walls. This distal supply tube 168 may reside within the catheter shaft 142, with the annulus between forming an aspiration lumen 160 (FIGS. 9-11). A strain relief 156 protects the catheter shaft 142 from kinking and other damage. In any cases in which luer fittings 154 are used (at any of the connections), a custom luer with an added o-ring may be used in order to allow the connection to withstand elevated pressures. In some embodiments, a bespoke connector may be utilized, to increase high pressure endurance. In some embodiments, pressures as high as 6.89 megapascal (1,200 pounds per square inch) or greater may be achieved without leakage or without causing decoupling of the catheter.

Figure 8:
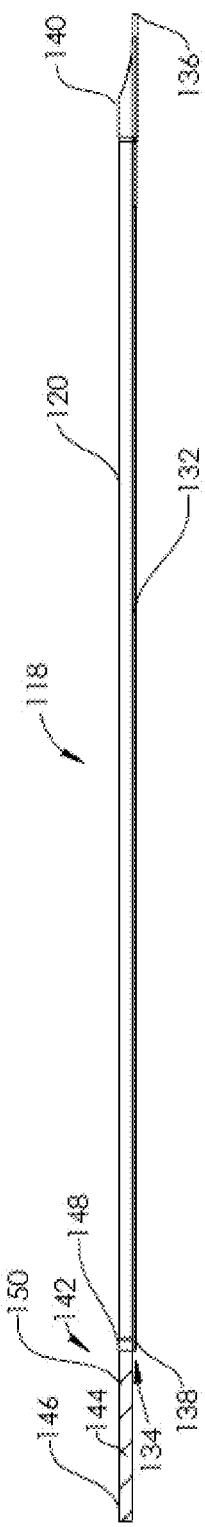
FIG. 8 is a detailed view of detail 8 of FIG. 4.

Turning to FIG. 8, the aspiration catheter 118 is illustrated as a single-operator exchange catheter and includes a guidewire tube 132 attached to the distal end 120 on one side of the aspiration catheter 118. The guidewire tube 132 can be between about 1 and about 30 cm in length, or between about 5 and about 25 cm in length, or between about 5 and about 20 cm in length, or approximately 13.5 cm in length. The guidewire tube 132 has a distal end 136 and a proximal end 138, and a single guidewire lumen 134 passing between the two ends 136, 138. The guidewire lumen 134 may be configured to be compatible with a 0.014" guidewire, a 0.018" guidewire, or a number of other guidewire diameters. A lumen inner diameter may be about 0.406 mm (0.016 inches) for compatibility with a 0.014" guidewire. The guidewire tube 132 may be constructed of a number of materials, including nylon, polyethylene, PEBAX®, polyester, PET, or may be constructed from composite or coextruded materials. For example an inner layer may comprise high density polyethylene or FEP, PTFE, ETFE, or other materials for high lubricity, and an outer layer may include PEBAX, nylon or other materials, for combination mechanical strength and flexibility. A tie layer may be used between the inner and outer layers, for example linear low density polyethylene. The catheter 118 may include a composite catheter shaft 142 having an inner support structure 144 covered with a polymer jacket 146. The inner support structure 144 may be a tubular braid or one or more helical coils, for example, made with stainless steel flat or round wires. The inner support structure 144 may also be spiral cut hypodermic tubing, for example made from 304 stainless steel or nickel-titanium. The spiral cut hypodermic tubing may have a pitch measuring about 4 to 6 millimeters, or about 5 millimeters at the proximal end for increased stiffness, transitioning to a pitch of about 0.75 to 1 mm or about 0.87 mm, at the distal end 150 of the inner support structure 144. In between the these two different pitch sections, may be intermediate pitch sections, for example, a section having a pitch of between about 2 mm and about 5 mm, and another section having a pitch of about 1 mm to about 2.5 mm. The inner support structure 144 may end at a transition zone 148, so that the polymer jacket 146 alone extends to the distal end 136 of the aspiration catheter 118. A catheter tip portion 140 is described in more detail in relation to FIGS. 9-11.

FIGS. 9-11 show an open distal end 158 of an aspiration lumen 160 for aspirating thrombus. A skive 162 may be formed in the polymer jacket 146, to aid entry of thrombus 164 that is aspirated into the aspiration lumen 160 (in the direction of arrow 180) by the combination of the vacuum created by the vacuum source 22. The skive 162 also minimizes the chances of the open distal end 158 being sucked against a blood vessel wall 166. A distal supply tube 168 has a closed distal end 170, for example, it may occluded during manufacture using adhesive, epoxy, hot melt adhesive or an interference member. Alternatively, the distal supply tube 168 may be closed off by melting a portion of it. The distal supply tube 168 has a lumen 176 extending its length and an orifice 172 formed through its wall 174 at a location adjacent and proximal to the closed distal end 170. The orifice 172 may have a diameter between about 0.0508 mm (0.002 inches) and about 0.1016 mm (0.004 inches), or about 0.0787 mm (0.0031 inches). The inner diameter of the distal supply tube 168 may be between about 0.3048 mm (0.012 inches) and about 0.4826 mm (0.019 inches), or between about 0.3556 mm (0.014 inches and about 0.4318 mm (0.017 inches) or about 0.3937 mm (0.0155 inches). The lumen 176 of the distal supply tube 168 is a continuation of an overall flow path emanating from the fluid source 20 including the extension tubing 122, the supply tube 130, the interior of the cassette 116, and the injection tube 152. In some embodiments, the lumen 176 of the distal supply tube 168 may taper, for example, from an inner diameter of about 0.3937 mm (0.0155 inches) at a proximal portion to an inner diameter of about 0.2974 mm (0.011 inches) at a distal portion. In some embodiments, the equivalent of a taper may be achieved by bonding different diameter tubing to each other, resulting in a stepped-down tubing inner diameter. In some embodiments, different diameter tapered tubing may be bonded to each other, for a combination of tapering and step-down of diameter. As described in conjunction with the piston pump, a pump output pressure wave of about 4.137 megapascal (600 pounds per square inch) to about 5.516 megapascal (800 pounds per square inch) causes a liquid injectate to flow through the flow path, including a the distal supply tube 168 (arrows 182), and causes a fluid jet 178 to exit the orifice 172 at a high velocity. The fluid jet 178, in absence of flow through the aspiration lumen 160 (for example if there is no vacuum), would impinge upon an inner wall 181 of the aspiration lumen 160 directly adjacent the orifice 172. Depending on the amount of vacuum present, the fluid jet, may curve as shown. The fluid jet 178 serves to macerate thrombus 164 that enters the aspiration lumen 160, and dilutes it. The flow rate of the liquid injectate (e.g. saline) and the amount of vacuum are controlled so that about 50% to about 70% of the volume of the mixture of the saline and blood flowing through the proximal aspiration lumen 160 is blood. Or about 60% of the volume is blood. This maceration and dilution assures that there is continuous flow through the aspiration lumen 160 so that it will not clog. The fluid jet 178 is configured to be contained within the aspiration lumen 160, and to not exit into a blood vessel or other body lumen.

Figure 14:
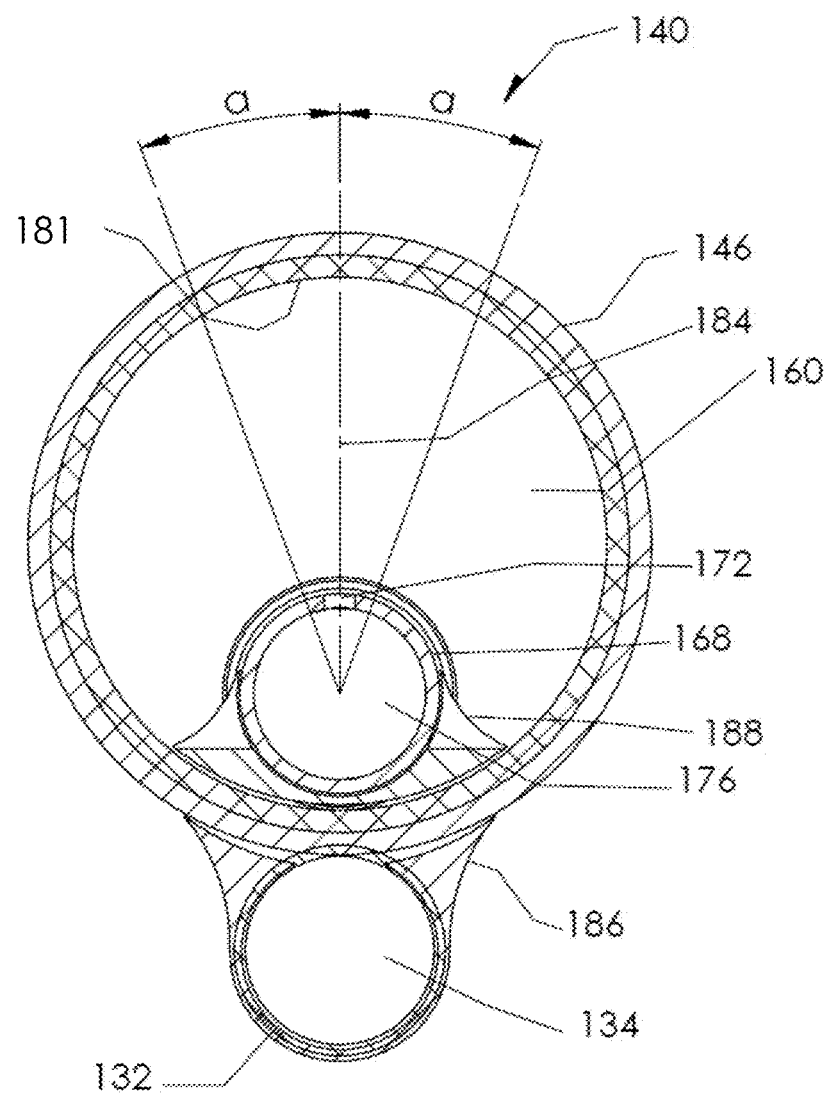
FIG. 14 is a cross-sectional view of the distal tip of the aspiration catheter of FIG. 9.

The axial center of the orifice 172 is about 0.3302 mm (0.013 inches) to about 0.4826 mm (0.019 inches) proximal to the most proximal portion of the open distal end 158, as illustrated by distance D in FIG. 11. FIG. 14 is a cross-section of the catheter tip portion 140 at the axial center of the orifice 172. The orifice 172 it is oriented approximately along a vertical midline 184 of the aspiration lumen 160, or within a range of ± a, there where angle a is about 20°. The angle a, may be varied in different embodiments between about 1° and about 45°, or between about 20° and about 35°. The guidewire tube 132 may be secured to the polymer jacket 146 with attachment materials 186, such as adhesive, epoxy, hot melt or other materials. The guidewire tube 132 may be secured along its entire length, or at discrete locations along its length, in order to maximize flexibility. The distal supply tube 168 may be secured within the aspiration lumen 160 with attachment materials 188, such as adhesive, epoxy, hot melt or other materials. The polymer jacket 146 may comprise a number of different materials, including PEBAX, nylon, or polyurethane. In some embodiments, the polymer jacket may be partially melt bonded to the distal supply tube 162 and/or the guidewire tube 132, in order to minimize the wall thickness of the assembly.

Turning to FIG. 8, the aspiration catheter 118 is illustrated as a single-operator exchange catheter and includes a guidewire tube 132 attached to the distal end 120 on one side of the aspiration catheter 118. The guidewire tube 132 can be between about 1 and about 30 cm in length, or between about 5 and about 25 cm in length, or between about 5 and about 20 cm in length, or approximately 13.5 cm in length. The guidewire tube 132 has a distal end 136 and a proximal end 138, and a single guidewire lumen 134 passing between the two ends 136, 138. The guidewire lumen 134 may be configured to be compatible with a 0.014" guidewire, a 0.018" guidewire, or a number of other guidewire diameters. A lumen inner diameter may be about 0.406 mm (0.016 inches) for compatibility with a 0.014" guidewire. The guidewire tube 132 may be constructed of a number of materials, including nylon, polyethylene, PEBAX®, polyester, PET, or may be constructed from composite or coextruded materials. For example, an inner layer may comprise high density polyethylene or FEP, PTFE, ETFE, or other materials for high lubricity, and an outer layer may include PEBAX, nylon or other materials, for combination mechanical strength and flexibility. A tie layer may be used between the inner and outer layers, for example linear low density polyethylene. The catheter 118 may include a composite catheter shaft 142 having an inner support structure 144 covered with a polymer jacket 146. The inner support structure 144 may be a tubular braid or one or more helical coils, for example, made with stainless steel flat or round wires. The inner support structure 144 may also be spiral cut hypodermic tubing, for example made from 304 stainless steel or nickel-titanium. The spiral cut hypodermic tubing may have a pitch measuring about 4 to 6 millimeters, or about 5 millimeters at the proximal end for increased stiffness, transitioning to a pitch of about 0.75 to 1 mm or about 0.87 mm, at the distal end 150 of the inner support structure 144. In between the these two different pitch sections, may be intermediate pitch sections, for example, a section having a pitch of between about 2 mm and about 5 mm, and another section having a pitch of about 1 mm to about 2.5 mm. The inner support structure 144 may end at a transition zone 148, so that the polymer jacket 146 alone extends to the distal end 136 of the aspiration catheter 118. A catheter tip portion 140 is described in more detail in relation to FIGS. 9-11.

Figure 15:
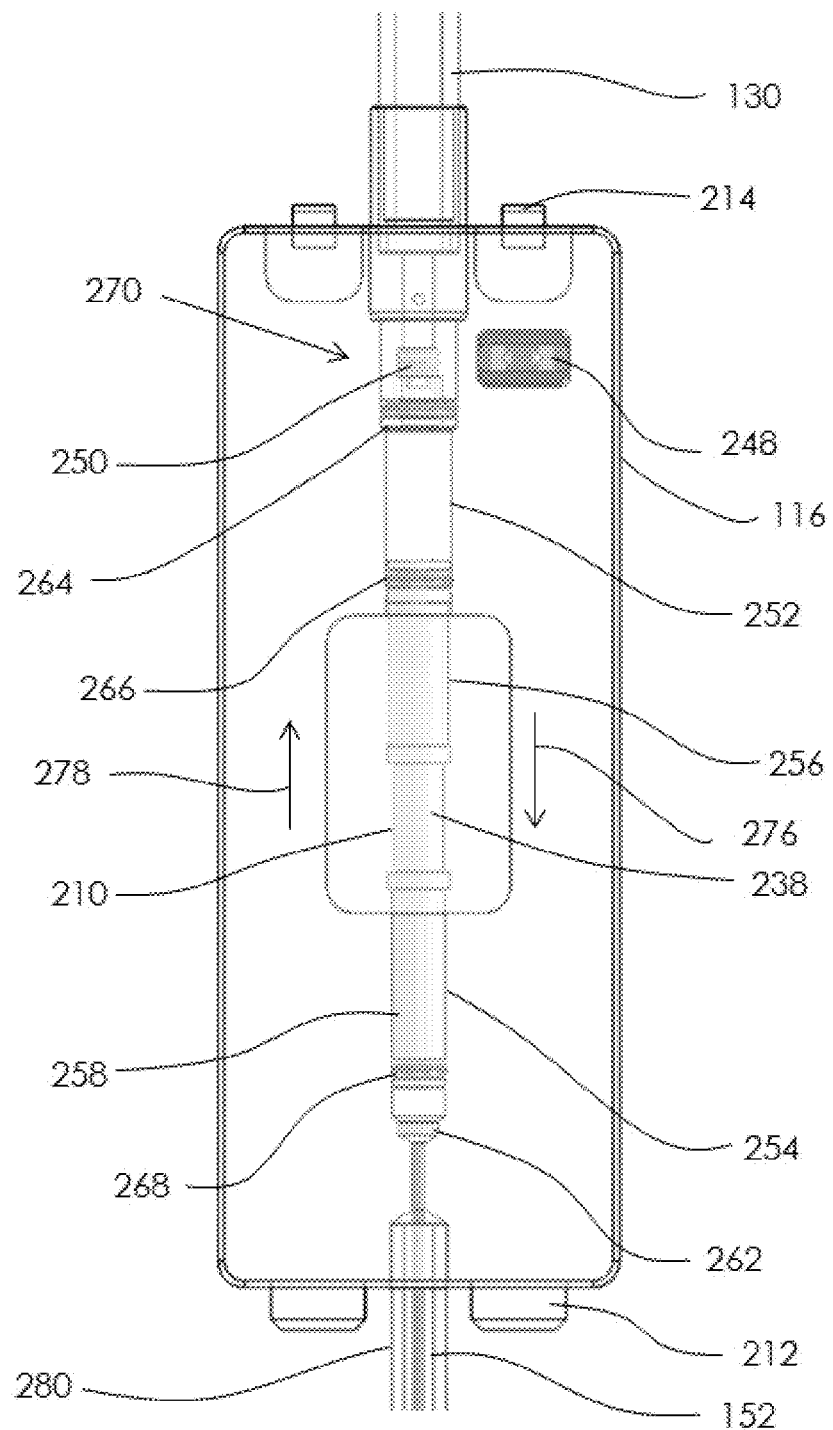
FIG. 15 is a view a cassette for coupling to a pump base.
Figure 16:
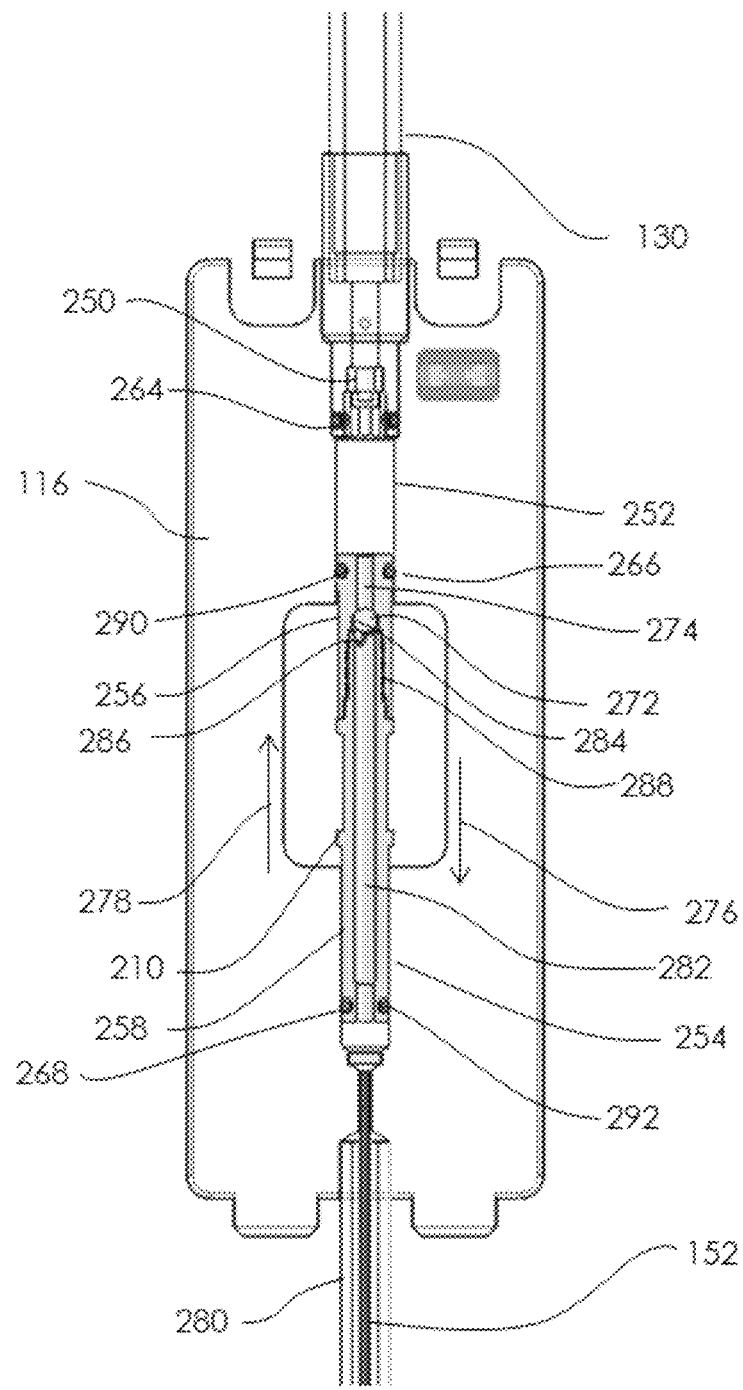
FIG. 16 is a sectional view of the cassette of FIG. 15.

FIGS. 15 and 16 illustrate the cassette 116 with most of its internal components visible. FIG. 16 is a sectional view of the cassette 116. The cassette 116 comprises an internal supply cylinder 252 and an internal injection cylinder 254, which are cylindrical cavities extending within the cassette 116. The piston 210 includes a supply side shaft 256 and an injection side shaft 258, the supply side shaft 256 including an o-ring 266 for sealably interfacing with the supply cylinder 252 and the injection side shaft 258 including an o-ring 268 for sealably interfacing with the injection cylinder 254. Each of the o-rings 266, 268 are within a cylindrical groove 290, 292 around each respective shaft portion 256, 258. An internal ball valve 272 (FIG. 16) stops injectate (saline) from flowing through an internal channel 274 in the supply side shaft 256 of the piston 210 when the piston 210 moves in a first direction 276, but the internal ball valve 272 allows injectate to flow through the internal channel 274 and through an internal channel 282 in the injection side shaft 258 when the piston 210 moves in a second direction 278. The ball valve 272 is axially held between a spherical annular recess 284 in the interior of the supply side shaft 256 and a recess having thru channels 286 in the injection side shaft 258. The supply side shaft 256 and the injection side shaft 258 may be held together with a threaded connection 288. When the piston 210 moves in the first direction 276, the injection side shaft 258 of the piston 210 and o-ring 268 force injectate through the injection tube 152. A protective tube 280 is shown over the injection tube 152. In FIG. 15, the injection side shaft 258 is shown at the bottom of an injection pulse. Injectate is filtered through an in-line filter 262, which may be a 40 to 50 micron filter, having an approximate thickness of 0.762 mm (0.030 inches). The in-line filter 262 is configured to keep particulate out of the injectate. Even though injectate is circulated through the aspiration catheter 118, and not into the blood vessel, the filtering provided by the in-line filter 262 is an extra safety step. However, this step helps assure that particulate does not block the small orifice 172 (FIG. 11). When the piston 210 moves in the second direction 278, the supply side shaft 256 of the piston 210 and the o-ring 266 sealably move together within the supply cylinder 252, but the ball valve 272 allows the injectate to pass through the internal channels 274, 282 of the piston 210 and fill the injection cylinder 254. The injectate is able to enter from the supply tube 130 through a check valve assembly 270 comprising an o-ring 264 and a check valve 250. The check valve 250 allows injectate to enter the interior of the cassette 116 from the supply tube 130, but not to move from the cassette 116 to the supply tube 130. The check valve 250 may be configured so that air, due at least in part to its low viscosity, will not be able to cause the check valve 250 to move (open), thus not allowing air to progress through the system. In some embodiments, the piston 210 may be a single piece (monolithic) design with a bore into which a check-valve is press-fit or bonded. A check valve compatible with this assembly may be supplied by the Lee Company of Westbrook, Conn., USA.

The volume of injectate injected per cycle may range from about 0.02 ml to about 41 ml, or from about 0.04 ml to about 2.0 ml, or about 0.06 ml to about 0.08 ml, or about 0.07 ml. The usable volume (volume that can be injected) of the injection cylinder 254 may be configured to be less than the usable volume (volume that can be filled from) of the supply cylinder 252, in order to assure sufficient filling of the injection cylinder 254. For example, the usable volume of the injection cylinder 254 may be about 0.05 ml to about 0.12 ml, and the usable volume of the supply cylinder 252 may be about 0.07 ml to about 0.16 ml. A usable volume ratio $R_U$ of between about 1.15 and about 2.00, or between about 1.25 and about 1.85, or about 1.40 is contemplated, where:

$$R_U = V_{SCU}/V_{ICU}, \text{ wherein:}$$

$V_{SCU}$=Usable volume of the supply cylinder 252, and
$V_{ICU}$=Usable volume of the injection cylinder 254.

A mean flow rate of between about 5 ml/minute and about 100 ml/minute. In some embodiments for use in coronary applications, 20 ml/minute may be desired. In some embodiments for use in peripheral applications, 50 ml/minute may be desired.

Figure 18:
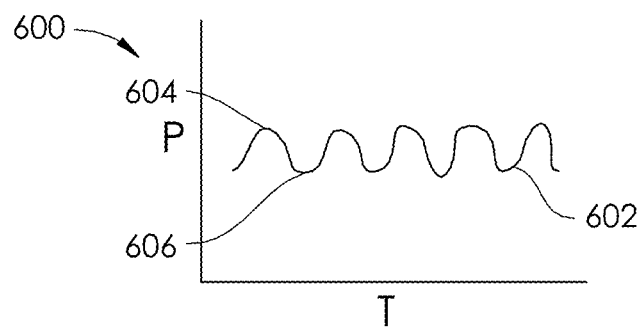
FIG. 18 is a graph of a pressure vs. time relationship of a piston pump.
Figure 19:
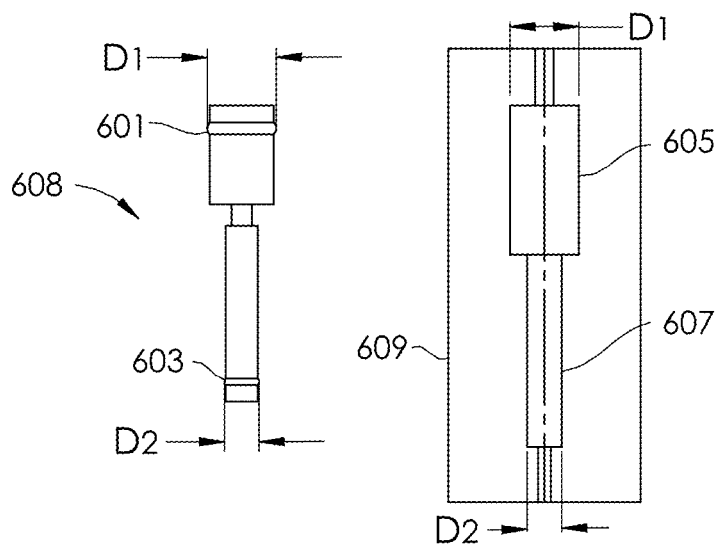
FIG. 19 is an elevation view of a piston and a cassette of a piston pump according to an embodiment of the present invention.
Figure 20:
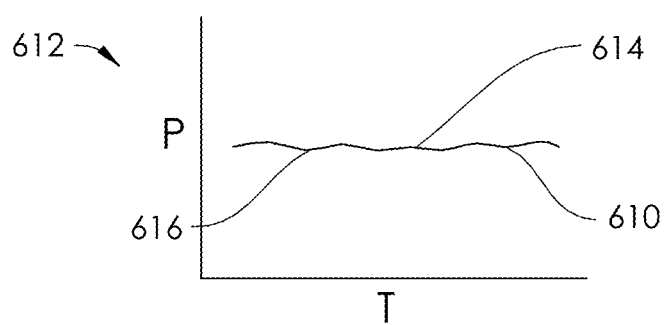
FIG. 20 is a graph of a pressure vs. time relationship of a piston pump.

FIG. 18 illustrates a graph 600 of a pressure (P) vs. time (T) curve 602 of a piston pump. Peaks 604 and valley 606 of the curve 602 can be dependent upon the design of the piston and cylinders of the piston pump, particularly of the usable volume ratio $R_U$. Turning to FIG. 19, a piston 608 is illustrated having a first diameter $D_1$ and a second diameter $D_2$ measured at the compressed o-rings 601, 603 (when placed within cylinders 605 and 607 of a cassette 609). The diameters of the cylinders 605, 607 are thus also defined as diameters $D_1$ and $D_2$. When the diameters $D_1$, $D_2$, and the lengths of the cylinders 605, 607 are adjusted such that the the usable volume ratio $R_U$ is optimized as previously described, a curve 610 as illustrated in FIG. 20 may be produced. The curve 610 has less-defined peaks 614 and valleys 616, and thus produces less variation of flow amplitude, and a more balanced injection.

Figure 17:
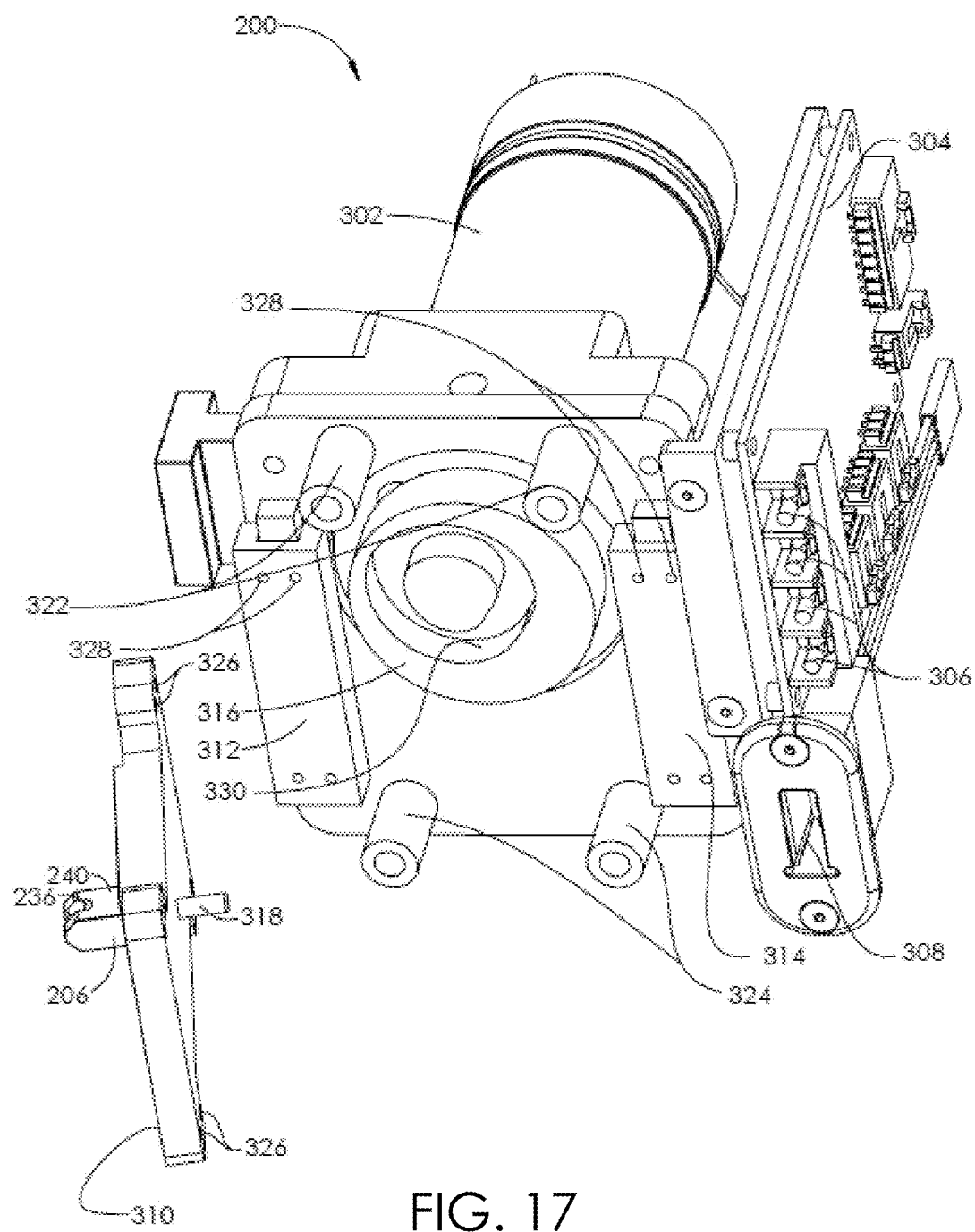
FIG. 17 is a partially exploded view of the pump base of FIG. 12.

The partially exploded pump base 200 in FIG. 17 illustrates the internal mechanisms for linear (up and down) actuation of the saddle 206, which is attached to a saddle stage 310. A motor 302 is controlled by a circuit board 304 and operated by the user interface 230 (FIG. 12), whose indicators 234 are lit by LEDs 306. The motor 302 turns a cam 316, in which includes a path 330. The saddle stage 310 has a pin 318 extending from its back side. The pin 318 may be press fit, bonded or screwed in place within the saddle stage 310. The saddle stage 310 is secured with screws to two slides 312, 314 through holes 326, 328, such that rotary motion of the cam 316 causes the pin 318 to track along the path 330 of the cam 316, thus causing the saddle stage 310 attached to the slides 312, 314 to slide upward and downward in cyclic motion. The shape of the cam determines the amount of acceleration and deceleration in the motion. Upper posts 322 and lower posts 324 serve as guides and/or stops of the saddle stage 310. The connector 114 of the pressure transducer 106 for measuring vacuum may be plugged into socket 308 (also shown in FIG. 12), and pressure related signals may be processed by the circuit board 304. The entire pump base 200 is reusable.

The inner contour diameter of the cam 316 may be sized and/or shaped to control the stroke length of the piston 210 and the amount of pulsatility (i.e., the difference between the high and low pressure). In some cases, decreasing the stroke length decreases the amount of pulsatiliy. In applications within the heart, such as coronary artery applications, lowering the amount of pulsatility can reduce the incidence of bradycardia. To compensate for a lower stroke length, and to maintain a sufficient total flow rate, the speed of the rotation of the cam (i.e. rotations per minute), can be increased, for example by increasing motor output speed, either by gearing or by increased applied voltage.

Figure 21:
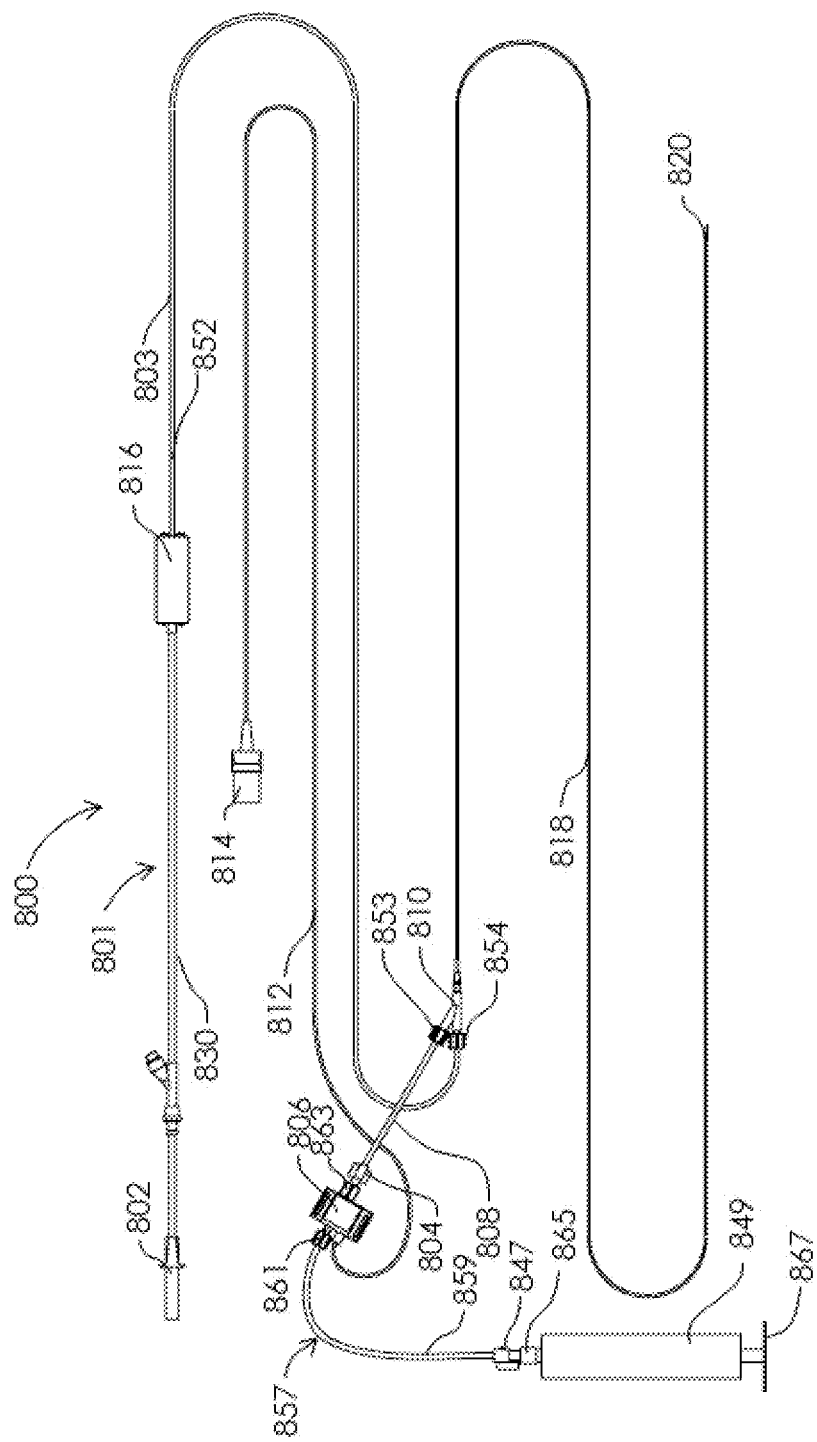
FIG. 21 is a plan view of disposable components of a system for aspirating thrombus according to an embodiment of the present invention.
Figure 22:
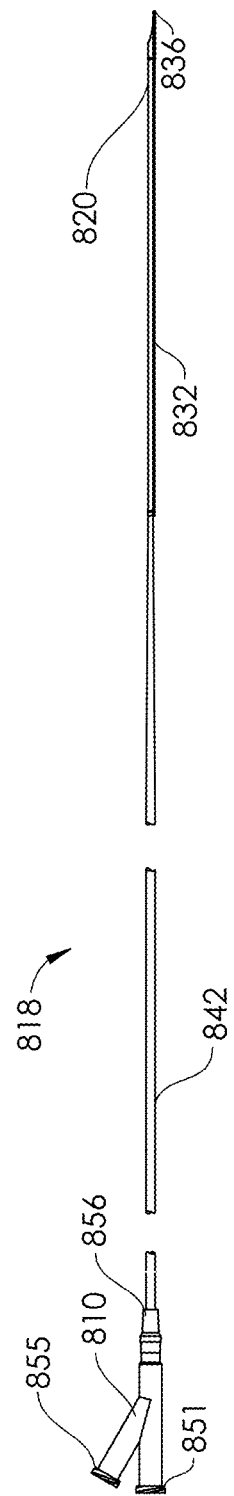
FIG. 22 is a detailed view of a catheter of the system for aspirating thrombus of FIG. 21.

Another embodiment of a system for aspirating thrombus 800 is illustrated in FIG. 21. The system for aspirating thrombus 800 includes, three major components: the pump base 200 of FIG. 12, an aspiration catheter 818, and a tubing set 803. The aspiration catheter 818 and the tubing set 803 represent disposable components 801, and the pump base 200 is a reusable component. It is not necessary to sterilize the pump base 200 as it is kept in a non-sterile field or area during use. The aspiration catheter 818 and the tubing set 803 may each be supplied sterile, after sterilization by ethylene oxide gas, electron beam, gamma, or other sterilization methods. The aspiration catheter 818 may be packaged and supplied separately from the tubing set 803, or the aspiration catheter 818 and the tubing set 803 may be package together and supplied together. Alternatively, the aspiration catheter 818 and tubing set may be packaged separately, but supplied together (i.e., bundled). As shown in FIGS. 21 and 22. The aspiration catheter 818 and tubing set 803 share many of the same features as the aspiration catheter 118 and tubing set 103 of FIG. 4, but are configured to allow easier separation from each other, and additional procedural adaptability. The aspiration catheter 818 has a distal end 820 comprising a guidewire tube 832 having a distal tip 836, and a proximal end 819 comprising a y-connector 810. The catheter shaft 842 of the aspiration catheter 818 is connected to the y-connector 810 via a protective strain relief 856. In other embodiments, the catheter shaft 842 may be attached to the y-connector 810 with a luer fitting. The y-connector 810 may comprise a first female luer 851 which communicates with a catheter supply lumen (as in the catheter 118 of FIGS. 4, 8-11), and a second female luer 855 which communicates with a catheter aspiration lumen (as in catheter 118 of FIGS. 4, 8-11).

Figure 23:
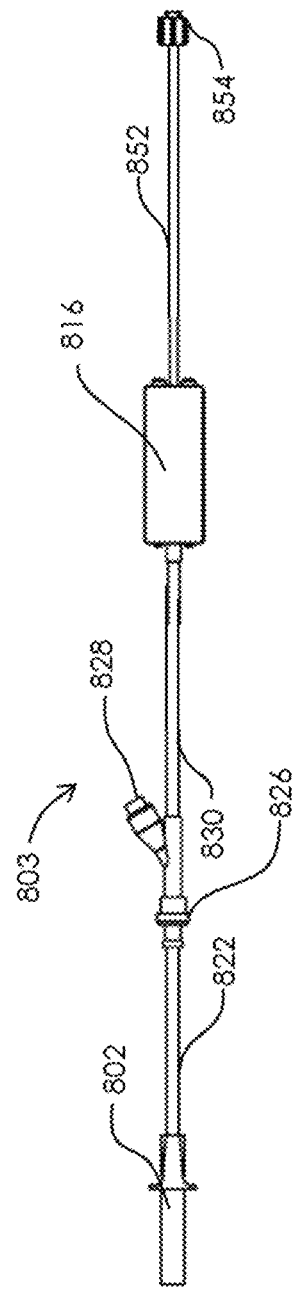
FIG. 23 is a detailed view of a tubing set of the system for aspirating thrombus of FIG. 21.

Turning to FIG. 23, the tubing set 803 is shown in more detail. A spike 802 for coupling to a fluid source 20 (FIG. 1) allows fluid to enter through extension tubing 822 and a check valve 826, and into supply tube 830. An optional injection port 828 allows injection of materials or removal of air, as described in relation to previous embodiments. A cassette 816 is used in conjunction with the pump base 200, and is similar in structure and function to the cassette 116 in FIGS. 15-16. Fluid is pumped into injection tube 852 from cassette 816. A male luer 854 is configured to attach to the female luer 851 of the y-connector 810.

Returning to FIG. 21, accessories 857 are illustrated that are intended for applying a vacuum source 22, including a syringe 849 having a plunger 867, to the catheter 818. The syringe 849 is attached to syringe extension tubing 859 via the luer 865 of the syringe 849. A stopcock 847 may be used to hold maintain the vacuum, or the plunger 867 may be a locking variety of plunger. A luer 861 of the syringe extension tubing 859 is connected to an pressure transducer 806, the pressure transducer 806 having a male luer 863 for connection to a connector (e.g., female luer) 804 of vacuum line 808. A male luer 853 at the end of the vacuum line 808 may be detachably secured to the female luer 855 of the y-connector 810 of the aspiration catheter 818. Signals from the pressure transducer 806 are carried through cable 812 to a connector 814. The connector 814 is plugged into the socket 308 (FIG. 12) of the pump base 200. Pressure related signals may be processed by the circuit board 304 of the pump base 200. The pressure transducer 806 may be power from the pump base 200, via cable 812. The accessories 857 may also be supplied sterile to the user.

FIG. 18 illustrates a graph 600 of a pressure (P) vs. time (T) curve 602 of a piston pump. Peaks 604 and valley 606 of the curve 602 can be dependent upon the design of the piston and cylinders of the piston pump, particularly of the usable volume ratio $R_U$. Turning to FIG. 19, a piston 608 is illustrated having a first diameter $D_1$ and a second diameter $D_2$ measured at the compressed o-rings 601, 603 (when placed within cylinders 605 and 607 of a cassette 609). The diameters of the cylinders 605, 607 are thus also defined as diameters $D_1$ and $D_2$. When the diameters $D_1$, $D_2$, and the lengths of the cylinders 605, 607 are adjusted such that the usable volume ratio $R_U$ is optimized as previously described, a curve 610 as illustrated in FIG. 20 may be produced. The curve 610 has less-defined peaks 614 and valleys 616, and thus produces less variation of flow amplitude, and a more balanced injection.

Figure 24:
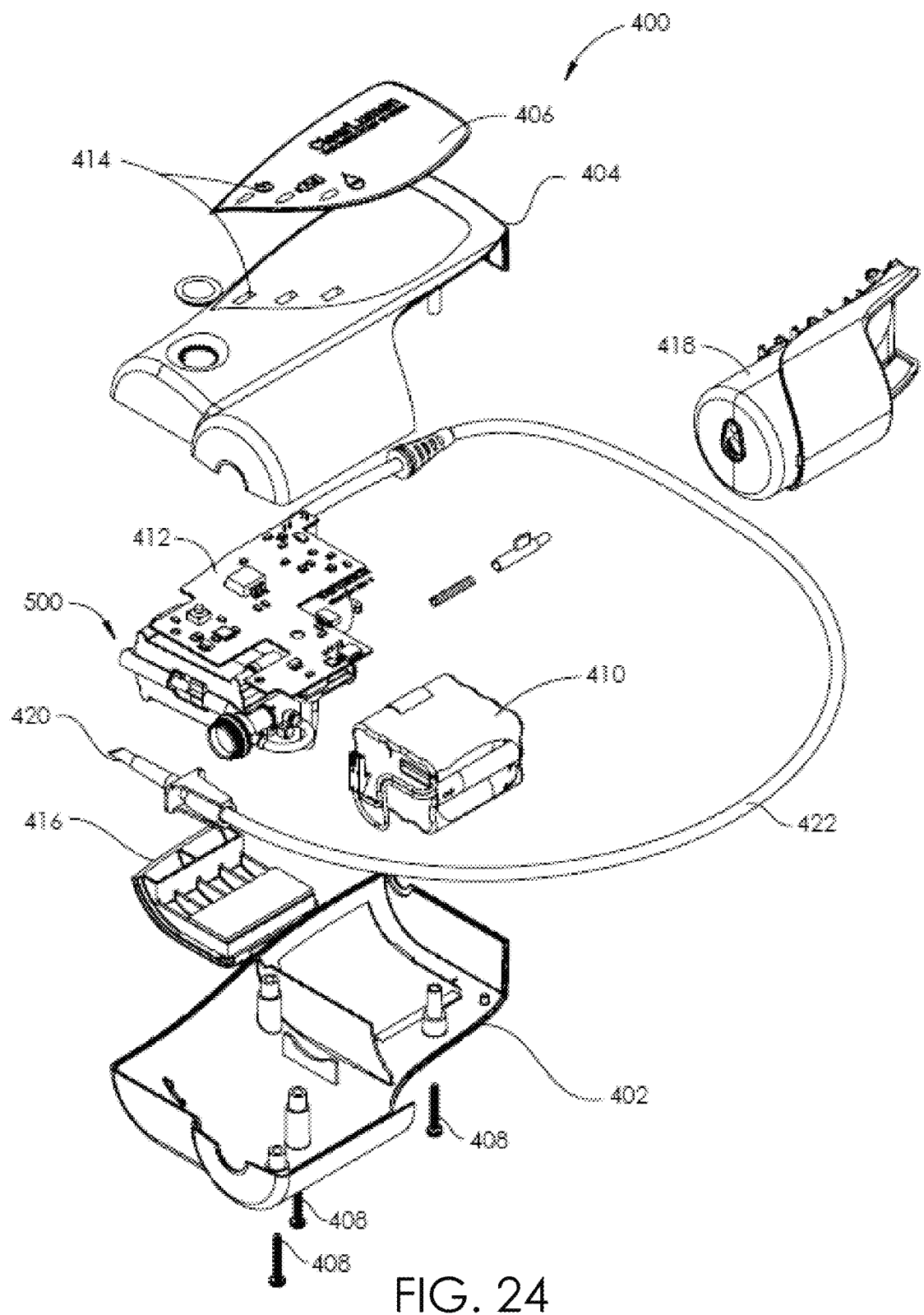
FIG. 24 is an exploded view of a saline pump drive unit according to an embodiment of the present invention.
Figure 25:
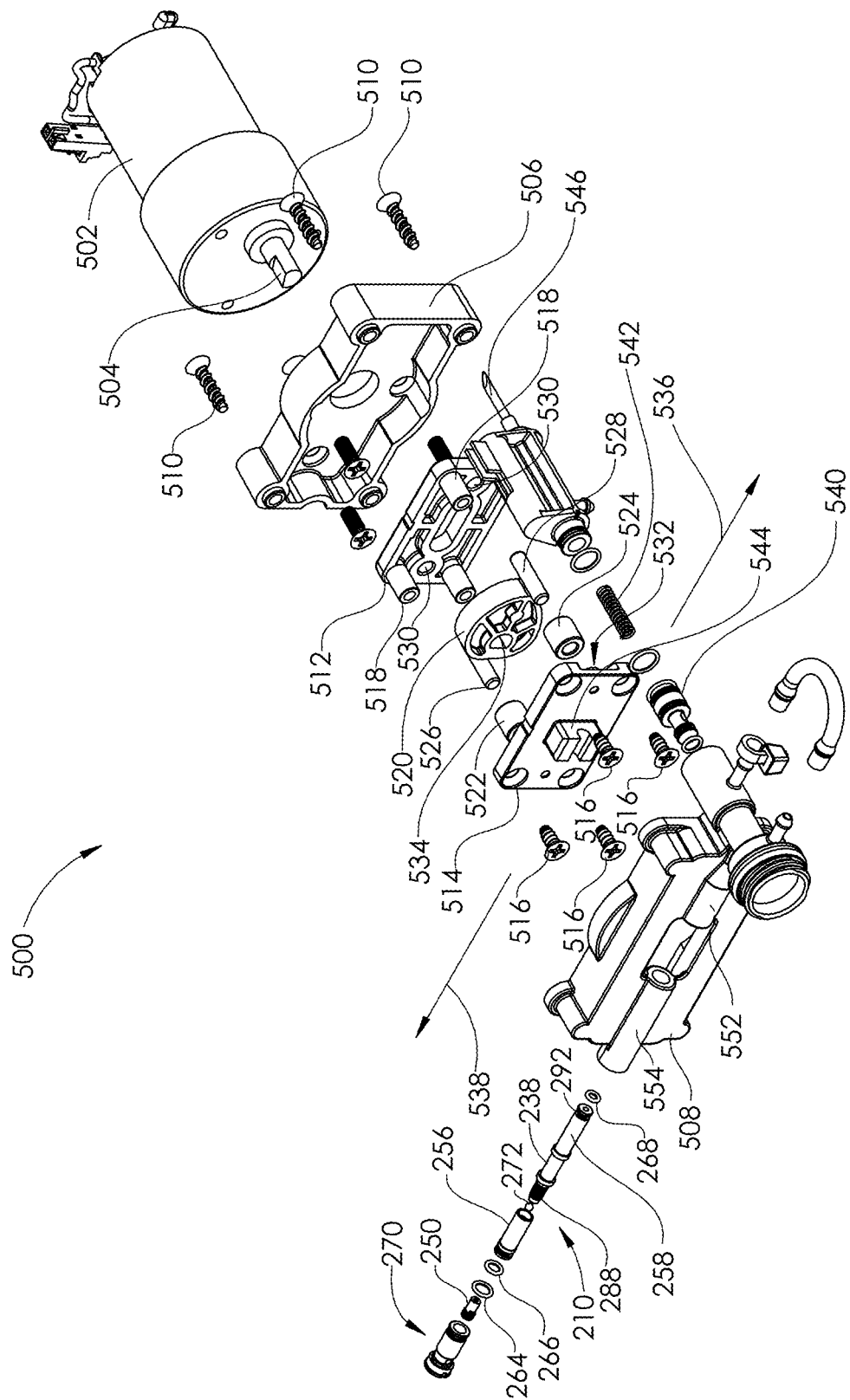
FIG. 25 is an exploded view of a disposable piston pump head of the saline pump unit of FIG. 24.
Figure 26:
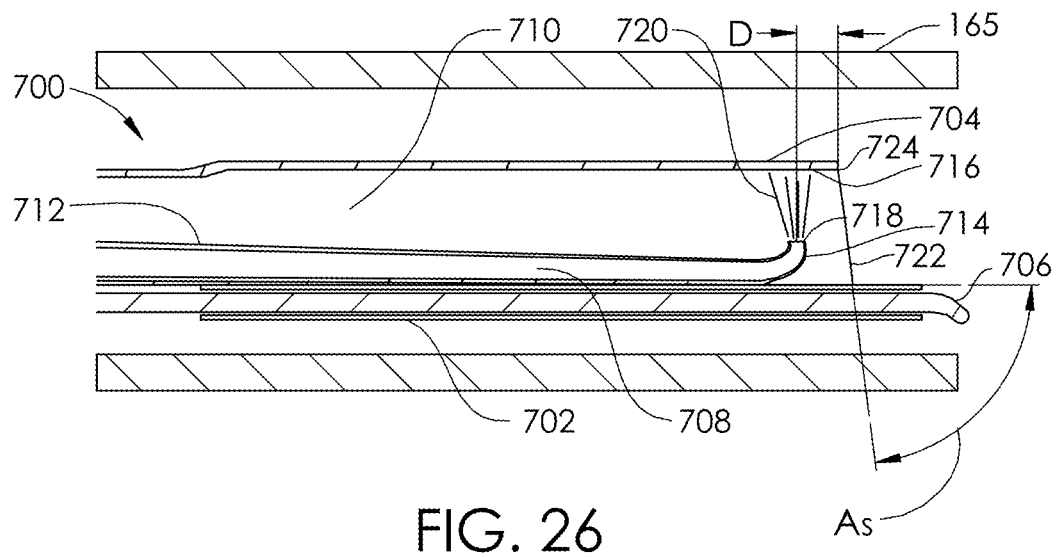
FIG. 26 is a sectional view of an aspiration catheter of a system for aspirating thrombus within a blood vessel according to an embodiment of the present invention.
Figure 27:
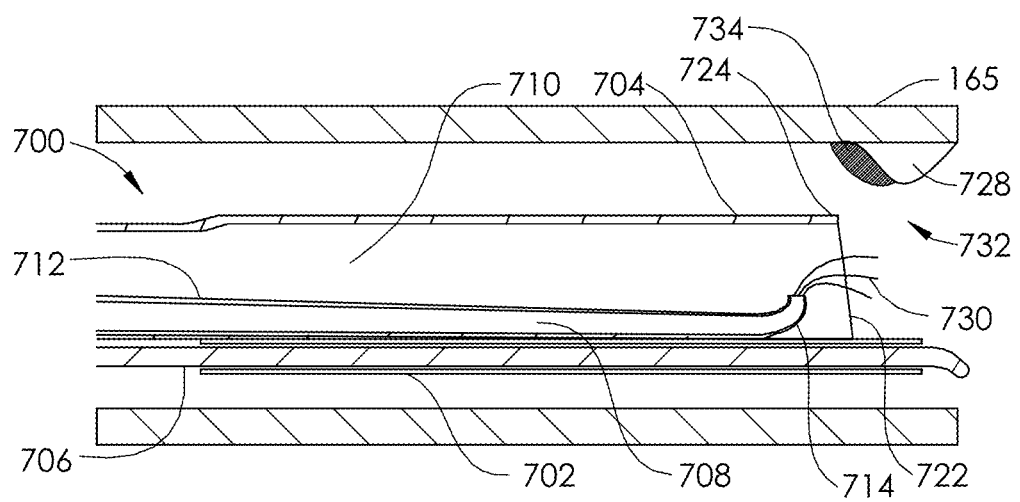
FIG. 27 is a sectional view of a catheter within a blood vessel delivering a drug to a target site.

FIGS. 24 and 25 illustrate a saline pump drive unit 400 having a completely disposable pump head 500. The saline pump drive unit 400 is configured to be usable with the catheters 16, 118 described herein, or other embodiments of aspiration systems comprising fluid injection. In FIG. 24, a bottom case 402 and a top case 404 having a label 406 are secured together with screws 408. Contained within the bottom case 402 and top case 404 are a battery pack 410 and an electronic control module 412. A battery cover 416 holds the battery pack 410 in place. In some embodiments, the battery pack 410 may supply a voltage of 18 Volts DC, but systems utilizing other voltages are possible. A user interface 414 enables operation of the saline pump drive unit. A vacuum bottle sleeve 418 may be used when a vacuum bottle is incorporated as the vacuum source 22. A spike 420 is connectable to a fluid source 20, and fluid injectate passes from the fluid source 20 through extension tubing 422 to a disposable piston pump head 500. Saline may be primed through the system by an automatic priming ("self-priming") system described herein in relation to prior embodiments, or may be primed by gravity from a saline bag that is located (for example on an IV pole) above the rest of the system. A valve on the lowest portion of the system may be opened in order to prime the entire system.

As illustrated in FIG. 25, the disposable piston pump head 500 is configured to couple to a motor shaft 504 of a motor 502, that is powered by the battery pack 410 of the saline pump drive unit 400. A motor plate 506 and a main body 508 of the disposable piston pump head 500 are secured to each other with screws 510, and hold the internal components of the disposable piston pump head 500. First and second follower plates 512, 514 are held together with screws 516 and bosses 518 extending from the first follower plate 512. The first and second follower plates 512, 514 rotatably hold a cam 520. The cam may be assymetric (as illustrated) or alternatively may be symmetric. The asymmetry may be incorporated in order to control the amount of noise in the pump, the contours serving to customize the shape of the pressure wave, and of the function of the pump. First and second bushings 522, 524 are rotatably held on first and second pins 526, 528. The pins 526, 528 insert into cylindrical cavities 530, 532 in each of the follower plates 512, 514.

In use, a user attaches the disposable piston pump head 500 to the motor 502 of the saline pump drive unit 400 by bringing the motor plate 506 close to the motor shaft 504 so that a d-shaped hole 534 in the cam 520 can be pressed over the d-shaped motor shaft 504. Alternatively, the d-shapes may be other non-circular shapes, including, but not limited to elliptical, oval, or rectangular. In operation the motor 502 turns the motor shaft 504, which in turn turns the cam 520. The cam 520 turns, forcing the bushings 522, 524 to push the first and second follower plates 512, 514 back and forth in a first direction 536 and a second direction 538. A saddle 544 is carried on the second follower plate 514, and a piston 210 may be coupled to the saddle 544 in the same manner as described herein with other embodiments. A supply cylinder 552 and an injection cylinder 554 in the main body 508 are analogous to the supply cylinder 252 and injection cylinder 254 of the cassette 116 of the system 100. The piston 210 of the cassette 116 may be used in the disposable piston pump head 500. The labelled components related to the piston 210 in FIG. 25 are similar to those described in relation to the piston 210 in FIGS. 15 and 16. The outer diameter of the cam 520 may be sized and/or shaped to control the stroke length of the piston 210 and the amount of pulsatility (i.e., the difference between the high and low pressure). In some cases, decreasing the stroke length decreases the amount of pulsatiliy. In applications within the heart, such as coronary artery applications, lowering the amount of pulsatility can reduce the incidence of bradycardia. To compensate for a lower stroke length, and to maintain a sufficient total flow rate, the speed of the rotation of the cam (i.e. rotations per minute), can be increased, for example by increasing motor output speed, either by gearing or by increased applied voltage. A vacuum spike 546 is used for coupling to the vacuum source 22, for example a vacuum bottle held within the vacuum bottle sleeve 418. A vacuum switch valve 540, which is activated against the bias of a spring 542, may be used to allow pump activation. For example, the electronic control module 412 may be configured to initiate the operation of the motor 502 automatically when the vacuum switch valve 540 sends a signal corresponding to movement of the vacuum switch valve 540, which occurs when a significant vacuum is achieved. This control may be instead of or in addition to control from a vacuum pressure transducer, such as pressure transducer 106. The turning on of the vacuum may thus be used to simultaneously turn on the motor 502, so that a single input begins the operation of the saline pump drive unit 400. Additionally, a vacuum source 22 may be controlled by the electronic control module 412 (for example, by opening or closing a solenoid), when a minimum injectate pressure is measured by an additional pressure transducer. For example, when a pressure of about 0.62 megapascal (90 pounds per square inch) or greater is measured, the vacuum may be activated or communicated to the system. An advantage of the saline pump drive unit 400 is that the user is required only to assemble a single component onto the shaft 504 of the motor 502.

As previously described, the systems according to any of the embodiments of the present invention may be configured such that active flow of saline (or other) injectate is not possible without concurrent vacuum being applied for aspiration. Also, the systems may be configured such aspiration is not possible without saline (or other) injectate flow. The systems according to any of the embodiments of the present invention may be configured such that current driving the pump (for example the current driving the motor 302, 502) is monitored, or by any alternative monitoring method, such that when a change in condition occurs, for example, air in the injection system, or clogs in any of the catheter lumens or extension tubes, or leaks within the system, the system shuts down, in order to avoid events such as injection of air into the blood vessels, or catheter or system failure.

Returning to FIG. 21, accessories 857 are illustrated that are intended for applying a vacuum source 22, including a syringe 849 having a plunger 867, to the catheter 818. The syringe 849 is attached to syringe extension tubing 859 via the luer 865 of the syringe 849. A stopcock 847 may be used to hold maintain the vacuum, or the plunger 867 may be a locking variety of plunger. A luer 861 of the syringe extension tubing 859 is connected to a pressure transducer 806, the pressure transducer 806 having a male luer 863 for connection to a connector (e.g., female luer) 804 of vacuum line 808. A male luer 853 at the end of the vacuum line 808 may be detachably secured to the female luer 855 of the y-connector 810 of the aspiration catheter 818. Signals from the pressure transducer 806 are carried through cable 812 to a connector 814. The connector 814 is plugged into the socket 308 (FIG. 12) of the pump base 200. Pressure related signals may be processed by the circuit board 304 of the pump base 200. The pressure transducer 806 may be power from the pump base 200, via cable 812. The accessories 857 may also be supplied sterile to the user.

In use, the pump base 200 resides outside the sterile field. Because operation of the pump base 200 may be controlled by the presence or absence of a pressure, a user who is working in the sterile field may turn the pump on or off without touching the non-sterile pump base 200. For example, the pump may be started by placing a vacuum on the system (e.g., pulling the plunger 867 of the syringe 849). The pump may in turn be stopped by removing the vacuum on the system (unlocking the plunger 867 of the syringe 849 and allowing to release, or opening the stopcock 847). The syringe 849 or the combination syringe 849 and stopcock 847 may act as a sterile on/off button of the pump vase 200. Alternatively, the aspiration catheter 818 may be initially used without the pump base 200, with only aspiration being applied to the aspiration lumen. If in certain cases, if the aspiration lumen becomes clogged, the distal end 820 of the aspiration catheter 818 may be backed off of the thrombus, and the pump base 200 and tubing set 803 may be coupled to the aspiration catheter 818, to then operate with forced saline injection, for increased aspiration, and clear the aspiration lumen. This will also help stop any thrombus that is blocking the aspiration lumen from being inadvertently delivered into the blood vessel of the patient.

Some of the drugs 730 which may be delivered include thrombolytic agents (clot busting drugs), such as streptokinase, tissue plasminogen activator (t-PA), recombinant or genetically-engineered tissue plasminogen activator, tenecteplase (TNK), urokinase, staphylokinase, and reteplase. Alternatively, stem cells or "cocktails" containing stem cells may be delivered. In some cases, glycoprotein inhibitos (GPI's) may be injected through the supply lumen 708 of the aspiration catheter 700. Saline or other aqueous solutions may be delivered alone for selective dilution of blood at the target site 732. In some applications, a solution may be used which is capable of exhibiting a phase change, for example, when its pressure or temperature is changed. In these applications, a liquid may be injected that becomes a gas when exiting from a small orifice, for example at the open end 718 of the supply lumen 708. Alternatively, a gas may be injected that becomes a liquid when being force through a small orifice, such as the open end 718 of the supply lumen 708. In any of the applications in which drugs 730 or other materials are injected intravascularly through the catheter 700, the injection of the drugs 730 or other materials may occur before, during, after, or instead of an aspiration procedure. Returning to the aspiration catheter 818 of FIGS. 21-22, if, during an aspiration procedure, it is desired to deliver drugs down the supply lumen and into the vessel, the tubing set 803 may be removed from the aspiration catheter 818 by disconnecting the male luer 854 of the tubing set 803 from the female luer 851 of the aspiration catheter 818, and the drug may be injected directly into the supply lumen at the female luer 851, for example, by a syringe or metering system, including a syringe/syringe pump combination. By also removing the vacuum source from the female luer 855 of the aspiration catheter 818, when aspiration lumen now serves as an overflow, so that the fluid being delivered into the patient (e.g., intravascularly) is maintained at a controlled rate. The volume of the supply lumen is relatively very small, so only a small volume of drug is needed to fill the supply lumen, and thus reach the distal top of the aspiration catheter 818. This, at the end of the procedure, very little drug is wasted, or needs to be disposed, allowing for a very cost-effective procedure.

In the embodiments described herein, a sterile fluid path is provided extending all the way from the fluid source 20 to the distal opening 40/open distal end 158 of the catheter 16, 118. In both the embodiments of the system 100 of FIGS. 4-17, the system 800 of FIGS. 21-23, and the embodiments of FIGS. 24-25, a disposable catheter and disposable pump set are configured to be supplied sterile, and coupled to a non-sterile (reusable) pump base 200 or pump motor 502. These combinations allow for reusability of the more expensive components, and for reusability (and maximized sterility) of the less expensive components, thus maximizing cost containment and patient safety at the same time.

In some cases, parts or all of the devices described herein may be doped with, made of, coated with, or otherwise include a radiopaque material. Radiopaque materials are understood to be materials capable of producing a relatively bright image on a fluoroscopy screen or another imaging technique during a medical procedure. Some examples of radiopaque materials can include, but are not limited to, gold, platinum, palladium, tantalum, tungsten alloy, polymer material loaded with a radiopaque filler, and the like. One or more hydrophilic or hydrophobic lubricious coatings may be used in order to improve trackability of the aspiration catheter 118 through the blood vessels.

In some instances, a degree of MRI compatibility may be imparted into parts of the devices described herein. For example, to enhance compatibility with Magnetic Resonance Imaging (MRI) machines, it may be desirable to make various portions of the devices described herein from materials that do not substantially distort MRI images or cause substantial artifacts (gaps in the images). Some ferromagnetic materials, for example, may not be suitable as they may create artifacts in an MRI image. In some cases, the devices described herein may include materials that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some instances, some of the devices described herein may include a coating such as a lubricious coating or a hydrophilic coating. Hydrophobic coatings such as fluoropolymers provide a dry lubricity. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

In one embodiment of the present invention, a system for aspirating thrombus includes an aspiration catheter having a high pressure supply lumen and an aspiration lumen, the supply lumen having a proximal end configured to attach to a piston pump and a closed distal end, the aspiration lumen having a proximal end configured to attach to a vacuum source and an open distal end; a first orifice in a side wall of the supply lumen which communicates directly with the interior of the aspiration lumen, the first orifice located proximal to the open distal end of the aspiration lumen and adjacent the closed distal end of the supply lumen; the piston pump configured to generate a cyclic pressure cycle when attached to the supply lumen, wherein the first orifice creates a spray pattern at least in conjunction with a peak of the piston pump pressure cycle such that the spray pattern impinges on an interior wall of the aspiration lumen when a distal end of the aspiration catheter is immersed within an environment having a temperature of between about 36° C. and 38° C., such that the spray is at an angle of between about 20° in each direction of the vertical midline of the aspiration lumen.

Some of the drugs 730 which may be delivered include thrombolytic agents (clot busting drugs), such as streptokinase, tissue plasminogen activator (t-PA), recombinant or genetically-engineered tissue plasminogen activator, tenecteplase (TNK), urokinase, staphylokinase, and reteplase. Alternatively, stem cells or "cocktails" containing stem cells may be delivered. In some cases, glycoprotein inhibitors (GPI's) may be injected through the supply lumen 708 of the aspiration catheter 700. Saline or other aqueous solutions may be delivered alone for selective dilution of blood at the target site 732. In some applications, a solution may be used which is capable of exhibiting a phase change, for example, when its pressure or temperature is changed. In these applications, a liquid may be injected that becomes a gas when exiting from a small orifice, for example at the open end 718 of the supply lumen 708. Alternatively, a gas may be injected that becomes a liquid when being force through a small orifice, such as the open end 718 of the supply lumen 708. In any of the applications in which drugs 730 or other materials are injected intravascularly through the catheter 700, the injection of the drugs 730 or other materials may occur before, during, after, or instead of an aspiration procedure. Returning to the aspiration catheter 818 of FIGS. 21-22, if, during an aspiration procedure, it is desired to deliver drugs down the supply lumen and into the vessel, the tubing set 803 may be removed from the aspiration catheter 818 by disconnecting the male luer 854 of the tubing set 803 from the female luer 851 of the aspiration catheter 818, and the drug may be injected directly into the supply lumen at the female luer 851, for example, by a syringe or metering system, including a syringe/syringe pump combination. By also removing the vacuum source from the female luer 855 of the aspiration catheter 818, when aspiration lumen now serves as an overflow, so that the fluid being delivered into the patient (e.g., intravascularly) is maintained at a controlled rate. The volume of the supply lumen is relatively very small, so only a small volume of drug is needed to fill the supply lumen, and thus reach the distal top of the aspiration catheter 818. This, at the end of the procedure, very little drug is wasted, or needs to be disposed, allowing for a very cost-effective procedure.

In another embodiment of the present invention, a system for aspirating thrombus includes an aspiration catheter having a high pressure supply lumen and an aspiration lumen, the supply lumen having a proximal end configured to attach to a piston pump and a closed distal end, the aspiration lumen having a proximal end configured to attach to a vacuum source and an open distal end; a first orifice in a side wall of the supply lumen which communicates directly with the interior of the aspiration lumen, the first orifice located proximal to the open distal end of the aspiration lumen and adjacent the closed distal end of the supply lumen; the piston pump configured to generate a cyclic pressure cycle when attached to the supply lumen, wherein the first orifice creates a spray pattern at least in conjunction with a peak of the piston pump pressure cycle such that the spray pattern impinges on an interior wall of the aspiration lumen when a distal end of the aspiration catheter is immersed within an environment having a temperature of between about 36° C. and 38° C.; wherein the piston pump includes a supply cylinder, an injection cylinder and a piston, the piston configured to actuate into the supply cylinder while actuating out of the injection cylinder, causing the injection cylinder to increase its volume of a liquid injectate, the piston further configured to actuate into the injection cylinder while actuating out of the supply cylinder, causing the injection cylinder to decrease its volume by injecting the liquid injectate, and causing the liquid injectate to travel through the supply lumen of the aspiration catheter; wherein the piston is configured to engage with a saddle associated with the piston pump, the saddle configured for cyclic linear motion, wherein motion of the saddle in a first direction actuates the piston out of the supply cylinder and motion of the saddle in a second direction actuates the piston into the supply cylinder.

In another embodiment of the present invention, a system for aspirating thrombus includes an aspiration catheter having a high pressure supply lumen and an aspiration lumen, the supply lumen having a proximal end configured to attach to a piston pump and a closed distal end, the aspiration lumen having a proximal end configured to attach to a vacuum source and an open distal end; a first orifice in a side wall of the supply lumen which communicates directly with the interior of the aspiration lumen, the first orifice located proximal to the open distal end of the aspiration lumen and adjacent the closed distal end of the supply lumen; the piston pump configured to generate a cyclic pressure cycle when attached to the supply lumen, wherein the first orifice creates a spray pattern at least in conjunction with a peak of the piston pump pressure cycle such that the spray pattern includes a jet; wherein the piston pump includes a supply cylinder, an injection cylinder and a piston, the piston configured to actuate into the supply cylinder while actuating out of the injection cylinder, causing the injection cylinder to increase its volume of a liquid injectate, the piston further configured to actuate into the injection cylinder while actuating out of the supply cylinder, causing the injection cylinder to decrease its volume by injecting the liquid injectate, and causing the liquid injectate to travel through the supply lumen of the aspiration catheter; wherein a usable volume ratio $R_U$ between the supply cylinder and the invention cylinder is between about 1.15 and about 2.00. Additionally, the usable volume ratio $R_U$ may be between about 1.25 and about 1.85. Additionally, the usable volume ratio $R_U$ may be about 1.40.

In another embodiment of the present invention a method for delivery of a drug includes providing a catheter including a supply lumen and an aspiration lumen, the supply lumen having a distal end, the aspiration lumen configured to couple to a vacuum source and having an interior wall surface, and an open distal end, an orifice at or near the distal end of the supply lumen, in fluid communication with the interior of the aspiration lumen, the orifice located proximally of the open distal end of the aspiration lumen, wherein the orifice is configured to create a spray pattern when pressurized fluid is pumped through the supply lumen such that the spray pattern impinges on the interior wall surface of the aspiration lumen when a distal end of the aspiration catheter is immersed within an aqueous environment, providing a disposable tubing set having a first conduit configured to couple the supply lumen of the catheter to a fluid source, and a pump component associated with the first conduit and configured to detachably couple to a drive unit, such that motion from the drive unit is transferred to the pump component such that resultant motion of the pump component causes fluid from the fluid source to be injected through the supply lumen of the catheter, and through the orifice into the aspiration lumen, coupling the supply lumen of the catheter to a fluid source, wherein the fluid source contains at least a first drug for intravascular delivery, inserting the catheter within a blood vessel of a patient and advancing the catheter to a target site, coupling the pump component to a drive unit, and operating the drive unit to cause the pump component to inject at least some of the first drug in the region of the target site.

It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

While embodiments of the present invention have been shown and described, various modifications may be made without departing from the scope of the present invention. The invention, therefore, should not be limited, except to the following claims, and their equivalents. Embodiments of the present invention are contemplated to have utility in a variety of blood vessels, including but not limited to coronary arteries, carotid arteries, intracranial/cerebral arteries, inferior and superior vena cavae and other veins (for example, in cases of deep venous thrombosis), peripheral arteries, shunts, grafts, vascular defects, and chambers of the heart. This includes, but is not limited to, any vessel having a diameter of bout two mm or greater. An aspiration catheter 118 outer diameter of about seven French or less is contemplated for many of the applications, though in certain applications, it may be larger. In some embodiments, an aspiration catheter 118 diameter of about six French or less is contemplated. Embodiments of the present invention may even be used in non-vascular applications, for example body lumens or cavities having material accumulations that need to be macerated and/or removed.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication.

What is claimed is:

1. A method of aspirating thrombus, comprising:
    advancing a distal end of a catheter proximate a thrombus within a target vessel of a patient, the catheter positioned within a sterile field and comprising an irrigation lumen and an aspiration lumen, wherein the aspiration lumen has a distal opening and wherein the irrigation lumen has an orifice at or near its distal end and directed into the aspiration lumen, wherein the catheter is operably connected proximally to a control, an aspiration conduit operably connected to a vacuum source, an irrigation conduit operably connected to a fluid source and a fluid pump, and a control box, the fluid source, fluid pump, and control box all positioned outside of the sterile field and spaced apart from the control; and
    actuating the control without touching any one or more of the fluid source, fluid pump, and control box, thereby solely mechanically causing hydraulic coupling of the vacuum source to the aspiration lumen, and electrically causing activation of the fluid pump, such that the fluid pump injects fluid from the fluid source through the irrigation lumen while vacuum is being applied to the aspiration lumen, and delivering the vacuum and the fluid to the distal end of the catheter to aspirate the thrombus.

2. The method of claim 1, wherein actuating the control comprises actuating the control spaced along the aspiration conduit or the irrigation conduit.

3. The method of claim 1, wherein actuating the control comprises actuating a vacuum switch valve.

4. The method of claim 1, wherein actuating the control comprises actuating a pressure/vacuum valve.

5. The method of claim 1, wherein actuating a control comprises placing a vacuum on at least one of the aspiration conduit or the aspiration lumen.

6. The method of claim 5, wherein the vacuum source comprises a syringe, and wherein placing a vacuum on the at least one of the aspiration conduit or the aspiration lumen comprises pulling a syringe plunger of the syringe connected to the aspiration conduit.

7. The method of claim 5, wherein placing a vacuum on the at least one of the aspiration conduit or the aspiration lumen comprises closing a stopcock connected to the aspiration conduit.

8. The method of claim 1, further comprising actuating the control, thereby turning off both the vacuum source and fluid pump.

9. The method of claim 8, further comprising turning off both the vacuum source and fluid pump when a vacuum pressure within the aspiration conduit is greater than a threshold value.

10. The method of claim 9, wherein the vacuum pressure is sensed by a pressure transducer.

11. A method of aspirating thrombus using a sterile field control, comprising:
    advancing a distal end of a catheter proximate a thrombus within a target vessel of a patient, the catheter positioned within a sterile field and comprising an irrigation lumen and an aspiration lumen, wherein the aspiration lumen has a distal opening and wherein the irrigation lumen has an orifice at or near its distal end and directed into the aspiration lumen, wherein the catheter is operably connected proximally to a control, an aspiration conduit operably connected to a vacuum source, an irrigation conduit operably connected to a fluid source and a fluid pump, and a control box, the fluid source, fluid pump, and control box all positioned outside of the sterile field and spaced apart from the control; and
    actuating the control within the sterile field, thereby solely mechanically causing hydraulic coupling of the vacuum source to the aspiration lumen, and electrically causing activation of the fluid pump, such that the fluid pump injects fluid from the fluid source through the irrigation lumen while vacuum is being applied to the aspiration lumen, and delivering the vacuum and the fluid to the distal end of the catheter to aspirate the thrombus.

12. The method of claim 11, wherein actuating the control comprises actuating the control spaced along the aspiration conduit or the irrigation conduit.

13. The method of claim 11, wherein actuating the control comprises actuating a vacuum switch valve.

14. The method of claim 11, wherein actuating the control comprises actuating a pressure/vacuum valve.

15. The method of claim 11, wherein actuating a control comprises placing a vacuum on at least one of the aspiration conduit or the aspiration lumen.

16. The method of claim 15, wherein the vacuum source comprises a syringe, and wherein placing a vacuum on the at least one of the aspiration conduit or the aspiration lumen comprises pulling a syringe plunger of the syringe connected to the aspiration conduit.

17. The method of claim 15, wherein placing a vacuum on the at least one of the aspiration conduit or the aspiration lumen comprises closing a stopcock connected to the aspiration conduit.

18. The method of claim 11, further comprising actuating the control, thereby turning off both the vacuum source and fluid pump.

19. The method of claim 18, further comprising turning off both the vacuum source and fluid pump when a vacuum pressure within the aspiration conduit is greater than a threshold value.

20. The method of claim 19, wherein the vacuum pressure is sensed by a pressure transducer.

* * * * *